(12) United States Patent
Karasawa

(10) Patent No.: US 7,717,851 B2
(45) Date of Patent: May 18, 2010

(54) ULTRASONIC OBSERVATION APPARATUS HAVING MULTI-BEAM SCAN FUNCTION

(75) Inventor: Hiroyuki Karasawa, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1035 days.

(21) Appl. No.: 11/400,377

(22) Filed: Apr. 10, 2006

(65) Prior Publication Data

US 2006/0241482 A1  Oct. 26, 2006

(30) Foreign Application Priority Data

Apr. 11, 2005  (JP) .............................. 2005-112984

(51) Int. Cl.
*A61B 8/00* (2006.01)
(52) U.S. Cl. .................................... 600/447
(58) Field of Classification Search ................. 600/437, 600/440, 441, 462–471; 73/596, 609, 632; 367/153, 178, 189
See application file for complete search history.

(56) References Cited

U.S. PATENT DOCUMENTS

| 5,301,674 A | * | 4/1994 | Erikson et al. | ............. | 600/447 |
| 5,980,459 A | * | 11/1999 | Chiao et al. | .................. | 600/447 |
| 6,540,683 B1 | * | 4/2003 | Lin | ............................. | 600/447 |
| 6,629,929 B1 | * | 10/2003 | Jago et al. | .................... | 600/447 |
| 7,066,886 B2 | * | 6/2006 | Song et al. | ................... | 600/443 |

FOREIGN PATENT DOCUMENTS

| JP | 5-056980 A | 3/1993 |
| JP | 8-173420 A | 7/1996 |
| JP | 2001-170046 A | 6/2001 |
| JP | 2001-333902 A | 12/2001 |

OTHER PUBLICATIONS

The Experience of Electric Radial Endoscopic Ultrasonography on Gastroenterology.

* cited by examiner

*Primary Examiner*—Brian Casler
*Assistant Examiner*—Parikha S Mehta
(74) *Attorney, Agent, or Firm*—Sughrue Mion, PLLC

(57) ABSTRACT

An ultrasonic observation apparatus in which the frame rate can be made higher than that in a mechanical or conventional electronic scan method. The ultrasonic observation apparatus includes: an ultrasonic endoscope including ultrasonic transducers; a transmission aperture setting unit for setting ultrasonic transducer groups as transmission apertures; a transmission frequency setting unit for setting respective frequencies of drive signal groups for the transmission apertures; a drive signal generating unit for generating the drive signal groups having the set frequencies; a reception aperture setting unit for setting ultrasonic transducer groups as reception apertures; a signal processing unit for performing signal processing on reception signal groups respectively outputted from the ultrasonic transducer groups; and a control unit for controlling the transmission aperture setting unit to sequentially change regions of the ultrasonic transducer groups to be set as the transmission apertures at a predetermined time interval.

25 Claims, 23 Drawing Sheets

FIG.7
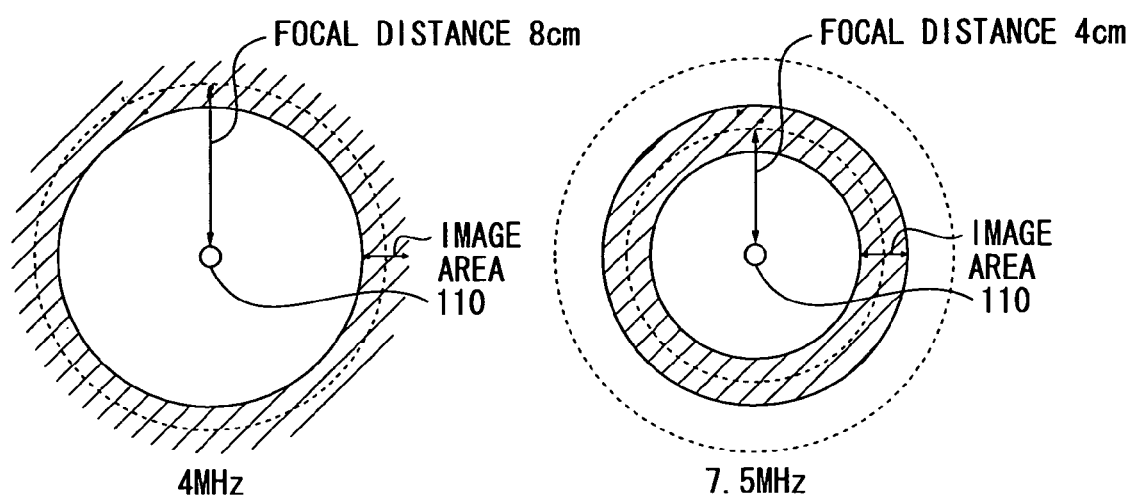
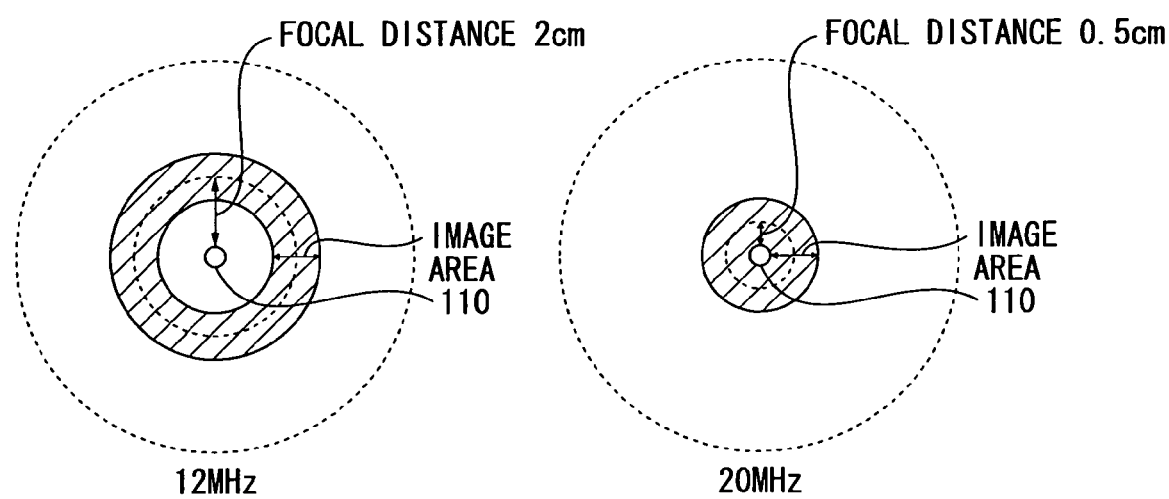

ULTRASONIC OBSERVATION APPARATUS HAVING MULTI-BEAM SCAN FUNCTION

BACKGROUND OF THE INVENTION

1. Field of the Invention

The present invention relates to an ultrasonic observation apparatus having an ultrasonic endoscope capable of being inserted into a body of a patient and taking ultrasonic tomographic images for medical diagnoses.

2. Description of a Related Art

Recent years, an ultrasonic endoscope to be used by being inserted into a body cavity of a patient has been developed for medical diagnoses based on ultrasonic tomographic images around the body cavity of the patient. In an ultrasonic endoscope, a mechanical radial scan method has been generally adopted which performs the scan with viewing angle of 360° by mechanically rotating an array including plural ultrasonic transducers (ultrasonic vibrators) for transmitting and receiving ultrasonic waves.

Further, an electronic radial scan method has been proposed which performs the scan with viewing angle of 360° by electronic scan. For example, Takeda et al., "The Experience of Electric Radial Endoscopic Ultrasonography on Gastroenterology", Jpn J Med Ultrasonics, Vol. 31, Supplement (2004), 77-C062 discloses results from studies on efficacy and problems of an electronic radial ultrasonic endoscope based on experiences in using the electric radial ultrasonic endoscope (ER-EUS) for various digestive system diseases.

Furthermore, in the radial scan method, acquisition of high quality ultrasonic images by simultaneously transmitting plural ultrasonic waves having frequencies different from one another in plural different directions has also been proposed.

As a related technology, Japanese Patent Application Publication JP-P2001-333902A discloses an ultrasonic diagnostic apparatus for obtaining plural pieces of echo data for observation by performing ultrasonic scan while varying an ultrasonic wave frequency. This ultrasonic diagnostic apparatus includes as main parts an ultrasonic observation unit, an image processing unit for performing various kinds of image processing, an ultrasonic probe having ultrasonic vibrators for transmitting and receiving ultrasonic waves, and a driving unit for driving the ultrasonic probe, and the ultrasonic vibrators are wideband vibrators such that driving frequencies can be changed (page 1). In the ultrasonic diagnostic apparatus, the ultrasonic observation unit includes a transmission and reception part for transmitting ultrasonic waves having different driving frequencies to the ultrasonic vibrators and receiving reflection waves of the ultrasonic waves, and a frame memory for receiving and storing the reflection waves as echo data. The selection among the various driving frequencies generated in the transmission and reception part is controlled by a system controller, and the selected driving frequency and echo data when employing the driving frequency are stored in association with each other.

Japanese Patent Application Publication JP-A-8-173420 discloses an ultrasonic image processing apparatus for synthesizing plural ultrasonic images having different frequency characteristics to make a smooth image and displaying the smooth image. This ultrasonic image processing apparatus includes ultrasonic transmitting and receiving means having different frequency characteristics from one another, control means for driving the plural ultrasonic transmitting and receiving means, and display means for weighting reception signals outputted from the plural ultrasonic transmitting and receiving means according to distances from positions within a screen corresponding to the ultrasonic transmitting and receiving means and synthesizing the reception signals to display the image in one screen (page 2).

Japanese Patent Application Publication JP-A-5-56980 discloses an ultrasonic diagnostic apparatus for easily performing frequency selection so as to deal with ultrasonic attenuation caused by higher frequency. This ultrasonic diagnostic apparatus includes an ultrasonic transducer shared among at least two center frequencies for obtaining reception signals by transmitting and receiving ultrasonic pulses having respective center frequencies, and means for independently collecting the reception signals for each center frequency by using the ultrasonic transducer (pages 1 and 2).

Japanese Patent Application Publication JP-P2001-170046A discloses a living tissue property diagnostic apparatus including signal analysis means for receiving an ultrasonic pulse reflected or transmitted within a living body and converting it into an electric signal, and diagnosing the living tissue property from an amount of characteristic of the electric signal in order to make correct diagnoses regardless of targets of measurement. In this living tissue property diagnostic apparatus, the signal analysis means has pulse width setting means for setting a pulse width of an electric signal, region extracting means for extracting plural signal regions which are different at least in part from one another, waveform characteristic value calculating means for calculating a predetermined waveform characteristic value in each of the extracted regions, difference computing means for computing the difference between the calculated waveform characteristic values, and corresponding time determining means for relating the result of the difference computation to the position of the living tissue that has generated the reception ultrasonic pulse by associating the result of the difference computation with the reception time of the ultrasonic pulse.

Thus, according to the mechanical or electronic radial scan method, there is an advantage that a wide viewing angle can be obtained. However, in comparison to a scan method of performing scanning with viewing angle of 90° by using a convex ultrasonic transducer array, for example, in the case where conditions of sound ray density, scan depth, and so on are set equal, there is a problem of reduction in frame rate because scan time (frame period) for obtaining an image for one frame becomes longer.

Further, as disclosed in JP-P2001-333902 and JP-A-8-173420, there is an advantage that the high resolving power (resolution) in the shallow part and penetration (focal depth) of ultrasonic waves to the deep part are consistent with each other by synthesizing plural ultrasonic images obtained by using ultrasonic waves having different frequencies from one another. However, in JP-P2001-333902 and JP-A-8-173420, only the mechanical radial scan method is used but it is not considered to use the electronic scan method.

On the other hand, JP-A-5-56980 suggests use of the electronic scan method when respectively transmitting plural ultrasonic waves having different frequencies from one another in plural different directions (page 3), but no specific aspect is revealed. In the case where the electronic scan method is adopted thereto, it is conceivable that the number of connecting lines to ultrasonic transducers becomes larger, but there is no disclosure about the measure against the problem. Also, there is no disclosure about combination of plural ultrasonic images obtained based on ultrasonic waves having different frequencies from one another to display the image, nor combination with an ultrasonic image generation method such as Doppler method other than B-mode image.

Further, JP-P2001-170046A does not specifically disclose an aspect of a probe to be used for extracting frequency components.

SUMMARY OF THE INVENTION

The present invention has been achieved in view of the above-mentioned problems. A first object of the present invention is to make a frame rate in an ultrasonic observation apparatus with an ultrasonic endoscope using an electronic radial scan method or convex scan method higher than that in a mechanical scan method or conventional electronic scan method. Further, a second object of the present invention is to generate ultrasonic images suitable for medical diagnoses based on ultrasonic image information obtained by transmitting and receiving ultrasonic waves having different frequency components from one another in such an ultrasonic observation apparatus.

In order to achieve the objects, an ultrasonic observation apparatus according to the present invention is an ultrasonic observation apparatus for acquiring ultrasonic image information on an object to be inspected by scanning the object in a body cavity thereof according to a radial scan method or convex scan method so as to generate an ultrasonic image based on the ultrasonic image information, and the apparatus comprises: an ultrasonic endoscope including plural ultrasonic transducers, arranged on a circumference or circular arc, for generating ultrasonic waves according to drive signals applied thereto and receiving the reflected ultrasonic waves to output reception signals, respectively; transmission aperture setting means for setting, from among the plural ultrasonic transducers, plural ultrasonic transducer groups for respectively transmitting plural ultrasonic beams in directions different from one another as plural transmission apertures; transmission frequency setting means for setting respective frequencies of drive signal groups to be supplied to the plural ultrasonic transducer groups set as the plural transmission apertures; drive signal generating means for generating the drive signal groups having the respective frequencies set by the transmission frequency setting means to supply the drive signal groups to the plural ultrasonic transducer groups set as the plural transmission apertures; reception aperture setting means for setting plural ultrasonic transducer groups as plural reception apertures corresponding to the plural transmission apertures; signal processing means for performing signal processing on reception signal groups respectively outputted from the plural ultrasonic transducer groups set as the reception apertures; and control means for controlling the transmission aperture setting means to sequentially change regions of the plural ultrasonic transducer groups to be set as the plural transmission apertures at a predetermined time interval.

According to the present invention, multi-beam scan is performed by transmitting plural ultrasonic beams substantially simultaneously according to a radial scan method or convex scan method in an ultrasonic endoscope, and therefore, the frame rate can be made higher than in a conventional scan method. Further, according to the present invention, plural ultrasonic beams having different frequencies from one another can be substantially simultaneously transmitted by setting respective frequencies of drive signals with respect to transmission apertures for transmitting the ultrasonic beams. Thereby, ultrasonic image information in which high resolving power is maintained in the shallow part and ultrasonic image information on the deep part can be acquired simultaneously. Therefore, the most appropriate ultrasonic images such as an image, in which plural B-mode images at different focal depths are synthesized, a harmonics image, a Doppler image, a frequency subtraction images, in which tissue properties are expressed, can be displayed according to diagnostic purposes, and the quality and efficiency of medical diagnoses can be improved.

BRIEF DESCRIPTION OF THE DRAWINGS

FIG. 7 shows image areas set according to the focal depths of the ultrasonic beams;

DESCRIPTION OF THE PREFERRED EMBODIMENTS

Figure 1:
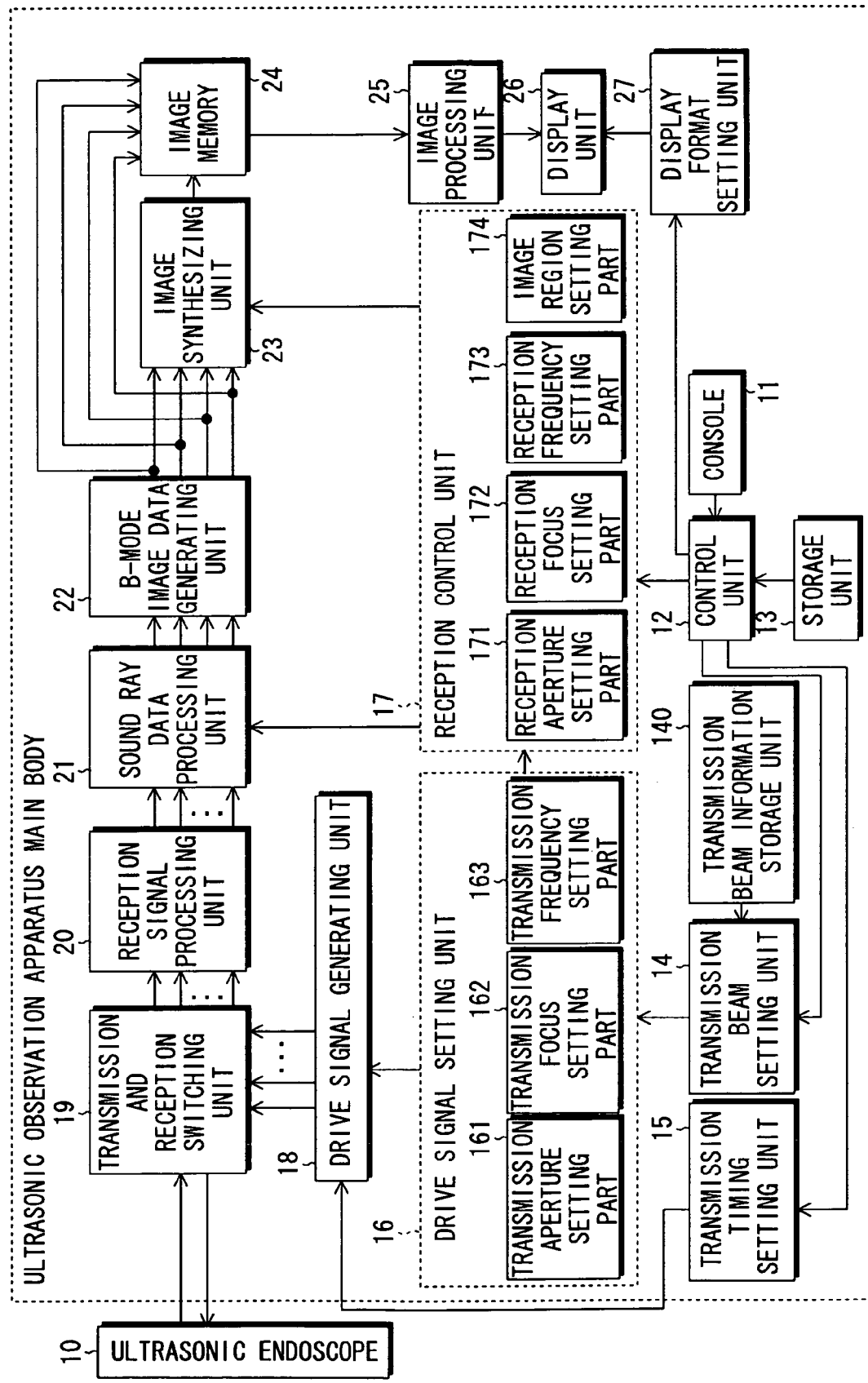
FIG. 1 is a block diagram showing a constitution of an ultrasonic observation apparatus according to the first embodiment of the present invention.

Hereinafter, preferred embodiments of the present invention will be explained in detail by referring to the drawings. The same reference numbers will be assigned to the same component elements and the description thereof will be omitted.

FIG. 1 is a block diagram showing a constitution of an ultrasonic observation apparatus according to the first embodiment of the present invention.

As shown in FIG. 1, the ultrasonic observation apparatus according to the embodiment includes an electronic radial ultrasonic endoscope 10 and an ultrasonic observation apparatus main body to which the ultrasonic endoscope 10 can be connected.

Figure 2:
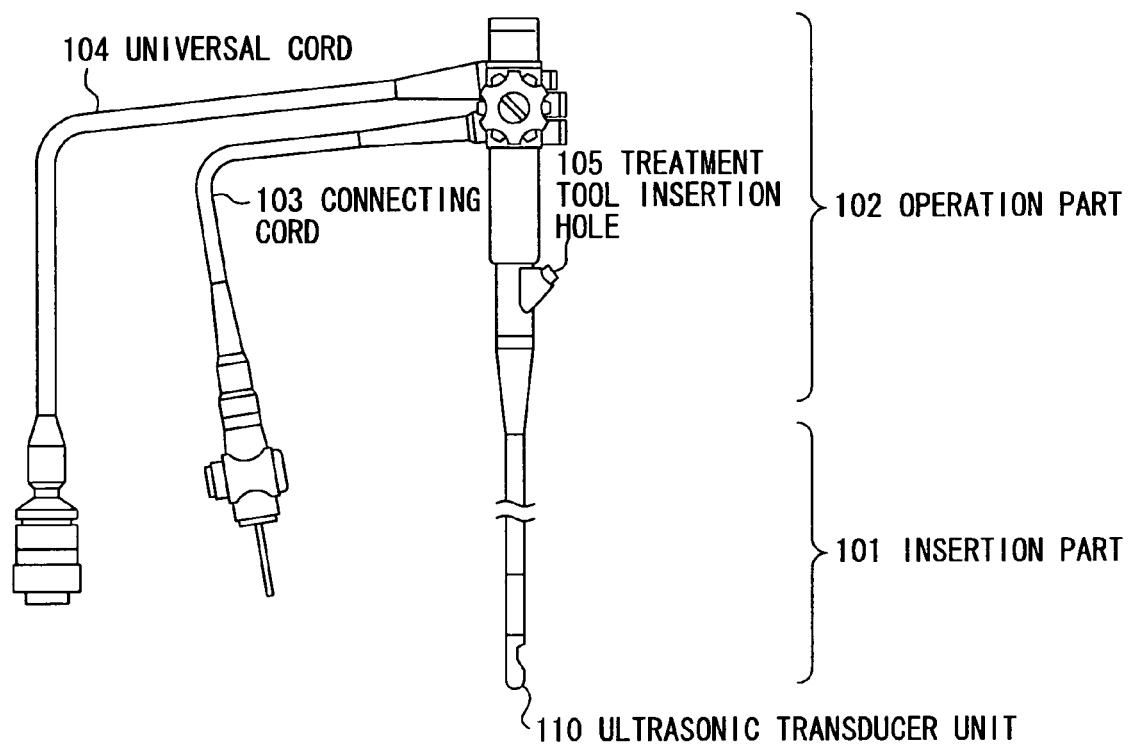
FIG. 2 is a schematic diagram showing a configuration of an ultrasonic endoscope shown in FIG. 1.

FIG. 2 is a schematic diagram showing a configuration of the ultrasonic endoscope 10 shown in FIG. 1. As shown in FIG. 2, the ultrasonic endoscope 10 includes an insertion part 101, an operation part 102, a connecting cord 103, and a universal cord 104.

The insertion part 101 of the ultrasonic endoscope 10 is an elongated flexible tube that can be inserted into a body of a patient. The operation part 102 is provided at the base end of the insertion part 101, connected to the ultrasonic observation apparatus main body via the connecting cord 103 and connected to a light source device via the universal cord 104. At the tip of the insertion part 101 of the ultrasonic endoscope 10, an ultrasonic transducer unit 110 in which plural ultrasonic transducers are arranged on the circumference thereof.

Figure 3:
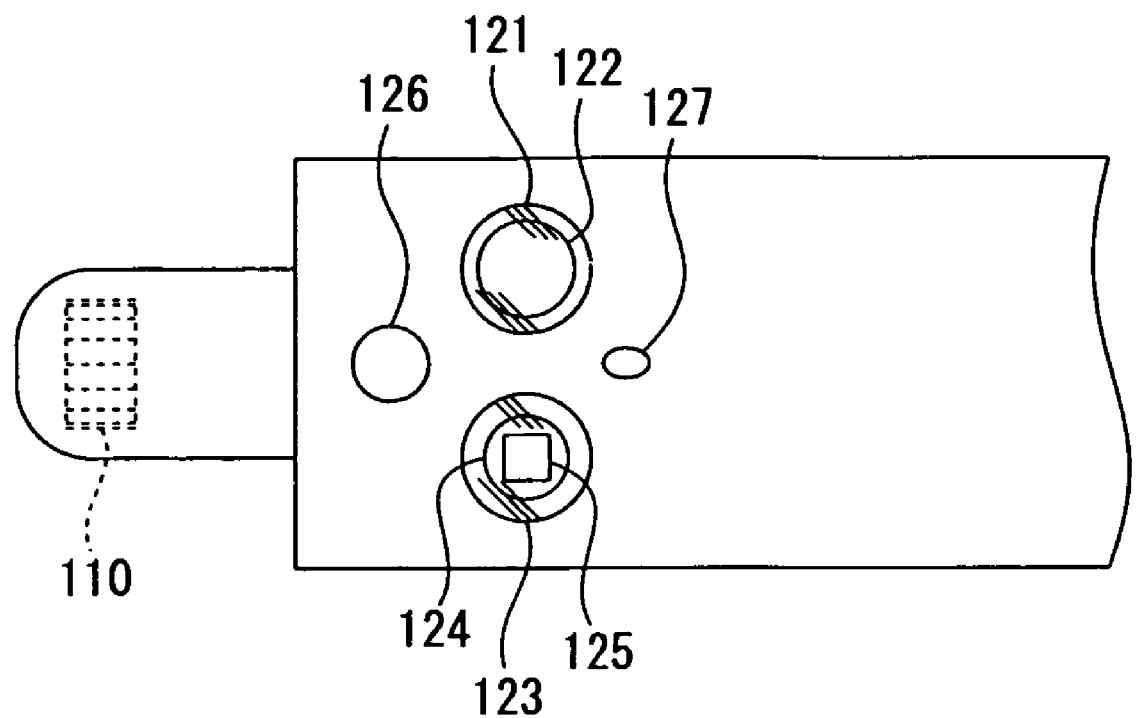
FIG. 3 is an enlarged view showing a tip of the ultrasonic endoscope shown in FIG. 2.

FIG. 3 is an enlarged view showing the tip of the ultrasonic endoscope 10 shown in FIG. 2.

At the tip of the ultrasonic endoscope 10, the ultrasonic transducer unit 110 is provided, and an illumination window 121, an observation window 123, a treatment tool lead-out hole 126, and a nozzle hole 127 are formed. An illumination lens 122 for outputting illumination light supplied via a light guide from the light source device is attached to the illumination window 121. These form an illumination optical system. Further, an objective lens 124 is attached to the observation window 123, and, in a position where the objective lens forms an image, a solid-state image sensor 125 such as an input end of an image guide or a CCD camera is disposed. These form an observation optical system.

The treatment tool lead-out hole 126 is a hole for leading out a treatment tool, etc. that has been inserted from a treatment tool insertion hole 105 (FIG. 2) provided to the operation part 102. Various treatments are performed in a body cavity of an object to be inspected by allowing a treatment tool such as forceps to be protruded from the hole and operating it by the operation part 102. Furthermore, the nozzle hole 127 is provided for supplying a liquid for cleansing the illumination window 121 and the observation window 123.

Figure 4:
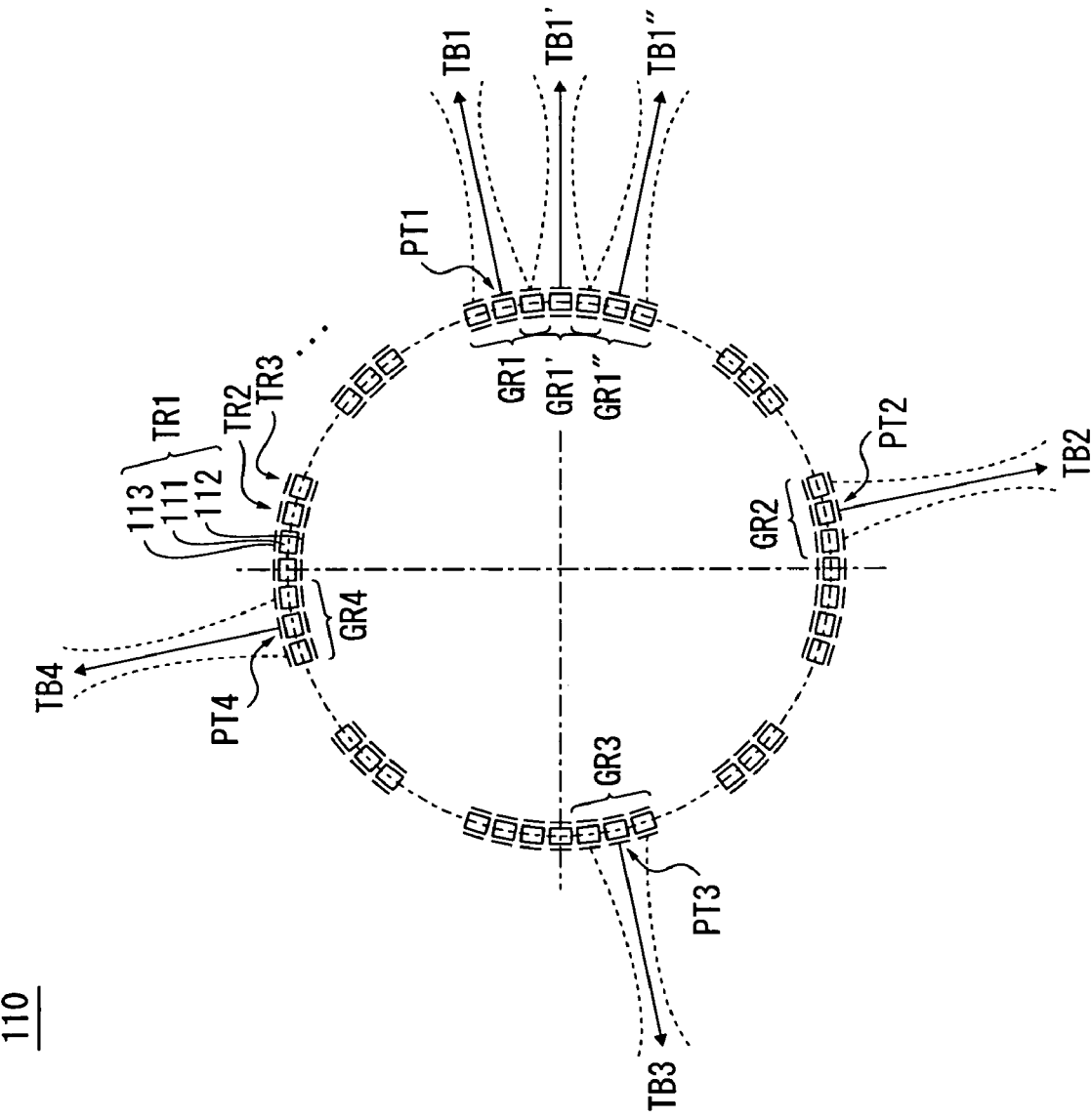
FIG. 4 is a top view showing an ultrasonic transducer unit shown in FIG. 3.

FIG. 4 is a top view showing the ultrasonic transducer unit 110 shown in FIG. 3. As shown in FIG. 4, the ultrasonic transducer unit 110 includes plural ultrasonic transducers TR1, TR2, . . . arranged on the circumference of the ultrasonic transducer unit 110. For example, 360 ultrasonic transducers TR1 to TR360 are arranged with a pitch of about 0.1 mm on the circumference of a circle having a diameter of about 11.5 mm.

Each of the ultrasonic transducers TR1 to TR360 is a vibrator having a wideband frequency characteristic with a frequency range from 4 MHz to 20 MHz. Each of the ultrasonic transducers TR1 to TR360 includes a piezoelectric material 111, and electrodes 112 and 113 disposed on both ends of the piezoelectric material 111. The piezoelectric material 111 is formed by piezoelectric ceramic represented by PZT (PB(lead) zirconate titanate), a polymeric piezoelectric element represented by PVDF (polyvinylidene difluoride), or the like. When driving signals are applied to such ultrasonic transducers TR1 to TR360, they expand and contract to generate ultrasonic waves. In this regard, the ultrasonic transducers TR1 to TR360 are driven while providing predetermined delay times, and thereby, ultrasonic beams to be transmitted in desired directions are formed. Further, the ultrasonic transducers TR1 to TR360 receive ultrasonic echoes generated in the object, convert the ultrasonic echoes into electric signals, and output the electric signals as reception signals.

In the ultrasonic transducer unit 110, ultrasonic transducer groups GR1, GR2, GR3, GR4 including adjacent plural ultrasonic transducers are set as transmission apertures and plural drive signals (drive signal groups) are supplied to the plural ultrasonic transducers included in the respective transmission apertures in a predetermined period, and thereby, plural ultrasonic beams TB1, TB2, TB3, TB4 are substantially simultaneously transmitted (multi-beam transmission). Further, the drive signal groups are sequentially supplied to the transmission apertures while the positions of the transmission apertures are shifted (e.g., GR1, GR1', GR1", . . . ), and thereby, the interior of the object is radially scanned by the multi-beam.

Referring to FIG. 1 again, the ultrasonic observation apparatus main body includes a console 11, a control unit 12, a storage unit 13, a transmission beam setting unit 14, a transmission timing setting unit 15, a drive signal setting unit 16, a reception control unit 17, a drive signal generating unit 18, a transmission and reception switching unit 19, a reception signal processing unit 20, a sound ray data processing unit 21, a B-mode image data generating unit 22, an image synthesizing unit 23, an image memory 24, an image processing unit 25, a display unit 26, and a display format setting unit 27.

The console 11 is operated by an operator for inputting various commands and information. The console 11 includes an input device such as a keyboard and touch panel, a pointing device such as a mouse, an adjust knob, an input button and so on. The console 11 outputs control signals for controlling start/stop of ultrasonic observation operation in the ultrasonic endoscope 10 and so on to the control unit 12.

The control unit 12 is constructed of a CPU (central processing unit) and software (program), and controls the respective units of the ultrasonic observation apparatus main body according to the control signals inputted from the console 11.

The storage unit 13 controls a recording medium for storing the program for actuating the CPU included in the ultrasonic imaging apparatus main body to perform operation, programs to be used for performing various kinds of processing, information to be used for those processing, and so on. As the recording medium, not only the built-in hard disk, but also an external hard disk, a flexible disk, an MO, an MT, a RAM, a CD-ROM, a DVD-ROM or the like may be used.

The transmission beam setting unit 14 sets the number, transmission positions and frequencies of ultrasonic beams subjected to multi-beam transmission under the control of the control unit 12. Further, as shown in FIG. 1, a transmission beam information storage unit 140 is provided for the transmission beam setting unit 14. The transmission beam information storage unit 140 stores suitable aperture widths, focal distances, beam diameters, drive signal waveforms and so on in correspondence with frequencies of ultrasonic beams, and the transmission beam setting unit 14 reads out the information from the transmission beam information storage unit 140 based on the frequencies of the ultrasonic beams to be transmitted. Furthermore, the transmission beam setting unit 14 sets intervals (angle intervals) between transmission positions according to the number of ultrasonic beams.

The transmission timing setting unit 15 sets transmission timing of ultrasonic beams or pulse repetition frequency (PRF) under the control of the control unit 12.

The drive signal setting unit 16 sets the ultrasonic transducers TR1, TR2, . . . (FIG. 4) to be driven and drive signals respectively provided to the ultrasonic transducers TR1, TR2, . . . based on the information read out from the transmission beam information storage unit 140 by the transmission beam setting unit 14. Specifically, a transmission aperture setting part 161, a transmission focus setting part 162 and a transmission frequency setting part 163 perform the following setting.

The transmission aperture setting part 161 sets plural ultrasonic transducer groups (ultrasonic transducer groups GR1 to GR4) included within the aperture widths with the transmission positions (positions PT1 to PT4 shown in FIG. 4) as centers based on the transmission positions and the aperture widths of the ultrasonic beams. Further, the transmission focus setting part 162 sets delay times (transmission focus setting) provided to plural drive signals to be respectively supplied to the plural ultrasonic transducers TR1, TR2, . . . included in each of the transmission apertures GR1 to GR4 in accordance with the focal depth of the ultrasonic beam. Furthermore, the transmission frequency setting part 163 sets frequencies of the drive signals to be respectively supplied to the plural ultrasonic transducers TR1, TR2 . . . with respect to the transmission apertures.

The reception control unit 17 controls the processing of reception signals outputted from the ultrasonic transducers and controls image data generation processing under the control of the control unit 12. Specifically, a reception aperture setting part 171, a reception focus setting part 172, a reception frequency setting part 173 and an image region setting part 174 perform the following setting.

The reception aperture setting part 171 sets plural reception apertures corresponding to the plural transmission apertures set by the drive signal setting unit 16. The ultrasonic transducer groups set as reception apertures may be the same as the ultrasonic transducer groups that are set as the transmission apertures, or may include other ultrasonic transducers in wider ranges than the ultrasonic transducer groups that are set as the transmission apertures.

The reception focus setting part 172 sets delay times (reception focus setting) provided to plural reception signals outputted from the plural ultrasonic transducers included in each of the reception apertures in correspondence with a frequency of the drive signal supplied to respective one of the transmission apertures. The delay times are used in reception focus processing, which will be explained later.

The reception frequency setting part 173 sets reception frequency bands with respect to the plural reception apertures in accordance with a frequency of the drive signal group supplied to the corresponding transmission aperture, that is, in accordance with a frequency of the transmitted ultrasonic beam. The reception frequency bands are used in reception filter processing, which will be explained later.

The image region setting part 174 sets suitable display ranges (image areas) of ultrasonic images generated based on reception beams in accordance with the focal depths formed in the reception beams by the reception focus processing. That is, since a predetermined depth range around the focal point is most clearly displayed in an image represented by the reception beams, the image area is set for cutting out such a depth range.

The drive signal generating unit 18 includes a number of pulsers corresponding to the number of ultrasonic transducers TR1 to TR360 included in the ultrasonic transducer unit 110 (FIG. 4). Each pulser generates a drive signal having a predetermined frequency based on the setting performed by the drive signal setting unit 16 in accordance with the transmission timing or PRF set by the transmission timing setting unit. Thereby, plural ultrasonic waves are respectively transmitted with predetermined time differences from the plural ultrasonic transducers included in each of the respective transmission apertures, and an ultrasonic beam are formed by adding those ultrasonic waves with a focal point formed at a predetermined depth.

The transmission and reception switching unit 19 switches between output of the drive signals generated in the drive signal generating unit 18 to the ultrasonic endoscope 10 and input of reception signals to the reception signal processing unit 20 with predetermined timing under the control of the control unit 12. By thus limiting the period for inputting reception signals, ultrasonic echoes produced by the reflection of the ultrasonic beams transmitted with predetermined timing at a certain depth of the object are detected.

Figure 5:
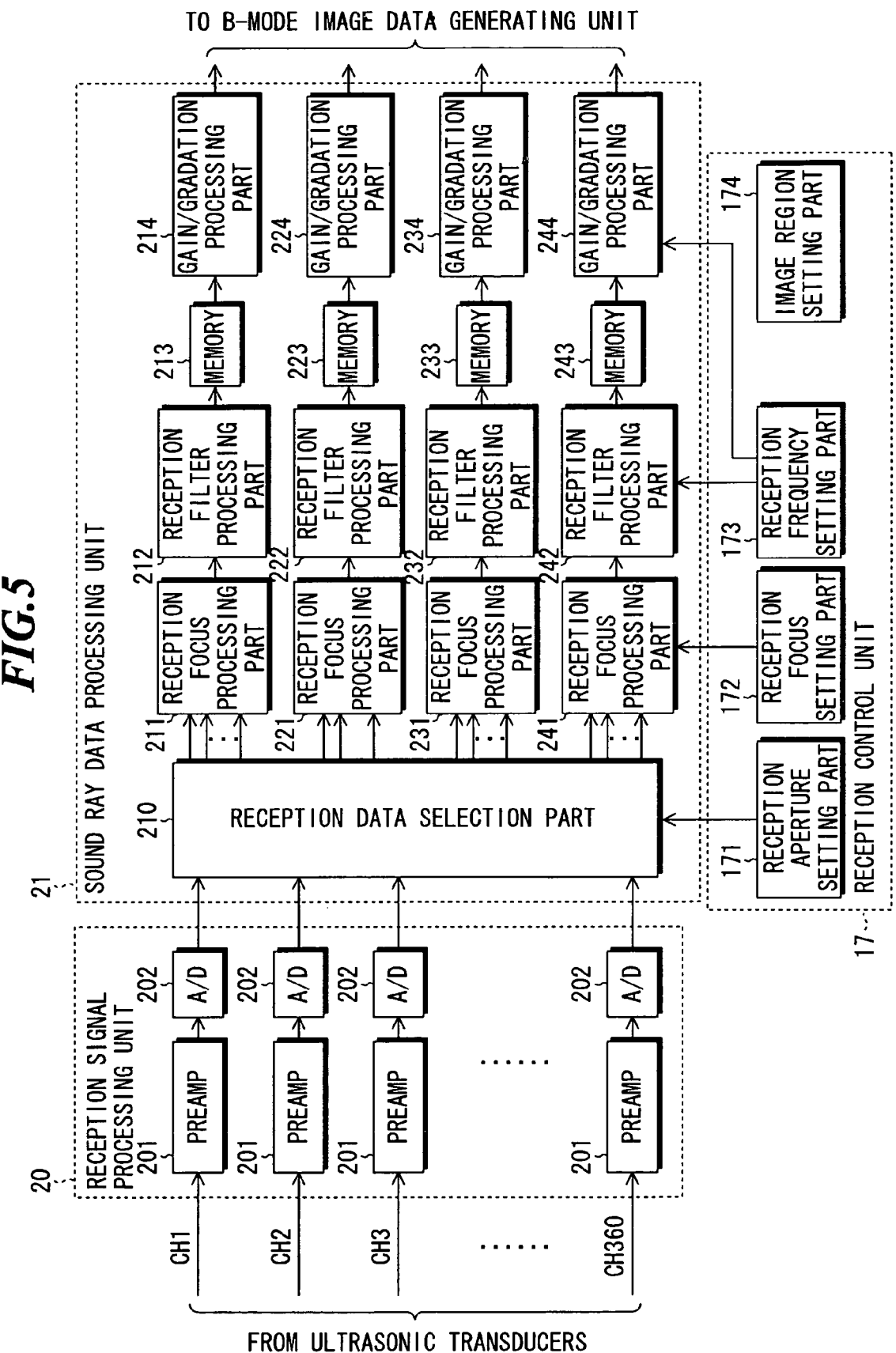
FIG. 5 is a block diagram showing a constitution of a reception signal processing unit and a sound ray data processing unit shown in FIG. 1.

FIG. 5 is a block diagram showing a constitution of the reception signal processing unit 20 and the sound ray data processing unit 21 shown in FIG. 1.

The reception signal processing unit 20 has plural channels CH1, CH2, . . . , CH360 corresponding to the plural ultrasonic transducers included in the ultrasonic endoscope 10. In each channel, a reception signal outputted from the ultrasonic transducer is preamplified by a preamplifier (PREAMP) 201, and subjected to analog/digital conversion by an A/D converter 202. Thereby, reception data representing ultrasonic image information received by each ultrasonic transducer is obtained. These pieces of reception data are inputted to a reception data selection part 210 of the sound ray data processing unit 21.

The sound ray data processing unit 21 includes the reception data selection part 210 and plural data processing systems provided according to the number of ultrasonic beams to be transmitted. In FIG. 5, four data processing systems 211-214, 221-224, 231-234 and 241-244 corresponding to four ultrasonic beams are shown.

The reception data selection part 210 selects reception data based on reception signal groups outputted from the ultrasonic transducer groups set as reception apertures in the reception aperture setting part 171 from among reception data outputted from the plural channels of the reception signal processing unit 20, and allows the selected reception data to data processing systems with respect to the reception apertures.

The respective data processing systems include reception focus processing parts 211-241, reception filter processing parts 212-242, memories (primary memories) 213-243 and gain/gradation processing parts 214-244.

Each of the reception focus processing parts 211-241 generates sound ray data in which a focal point is limited to a predetermined direction and a depth by providing delay times set in the reception focus setting part 172 to the inputted respective set of reception data and adding them.

Each of the reception filter processing parts 212-242 generates sound ray data in which the frequency is limited to a predetermined band by performing band-pass filter processing on the sound ray data generated by respective one of the reception focus processing parts 211-241 according to the reception frequencies set in the reception frequency setting part 173. Furthermore, each of the reception filter processing parts 212-242 performs envelope detection processing on the generated sound ray data and output the sound ray data subjected to the detection processing.

Each of the memories 213-243 sequentially stores the sound ray data outputted from respective one of the reception filter processing parts 212-242. After sound ray data for one frame (frame data) is accumulated in each of the memories 213-243, the frame data is outputted to respective one of the gain/gradation processing parts 214-244.

Each of the gain/gradation processing parts 214-244 makes correction of attenuation due to distance and gradation correction according to transmission frequency of the ultrasonic beam on the frame data outputted from respective one of the memories 213-243 under the control of the reception control unit 17. Here, the reason why the gradation correction is made with respect to reception apertures (i.e., corresponding transmission apertures) is that the reception sensitivity of the ultrasonic transducer for receiving ultrasonic echo changes depending on a frequency of the ultrasonic echo, i.e., a frequency of the transmitted ultrasonic beam.

Referring to FIG. 1 again, the B-mode image data generating unit 22 performs DSC (digital scan converter) processing for converting scan formats on the frame data generated by each of the data processing systems 211-214, 221-224, 231-234 and 241-244 of the sound ray data processing unit 21. Thereby, the sound ray data representing image information in a sound ray direction in the scan space of the ultrasonic beam is converted into image data for display in the physical space. That is, the B-mode image data generating unit 22 performs resampling corresponding to an image display range by performing coordinate transformation processing and interpolation processing corresponding to the radial scan method of the ultrasonic endoscope. Thereby, there are generated plural kinds of image data corresponding to the plural data processing systems 211-214, 221-224, 231-234 and 241-244 of the sound ray data processing unit 21, in other words, corresponding to the reception apertures or transmission apertures.

The image synthesizing unit 23 performs processing of synthesizing plural B-mode images at different focal depths based on the image areas set by the image region setting part 174 and the plural kinds of B-mode image data generated by the B-mode image data generating unit 22. Thereby, synthesized image data representing a synthesized B-mode image in which regions near focal points in the respective ultrasonic images are spliced is generated.

The image memory (secondary memory) 24 stores the plural kinds of B-mode image data generated by the B-mode image data generating unit 22 and the synthesized image data generated by the image synthesizing unit 23.

The image processing unit 25 performs necessary image processing such as linear gradation processing including gain adjustment and contrast adjustment and non-linear gradation processing including γ correction, converts the digital image data into an analog image signal, and outputs the image signal.

The display unit 26 includes a CRT display of raster scan type or an LCD display, and displays an ultrasonic image based on the image signal outputted from the image processing unit 25 according to the display format set by the display format setting unit 27.

The display format setting unit 27 sets one or plural image(s) to be displayed on a screen and a display format thereof from among the plural ultrasonic images represented by the plural kinds of B-mode image data and the synthesized image data under the control of the control unit 12. The kind and the display format of the image to be displayed are selected by an operator inputting a command by using the console 11. Specific display formats will be explained later.

Next, an ultrasonic observation method according to the first embodiment of the present invention will be explained. The ultrasonic observation method according to the embodiment is a method of acquiring ultrasonic image information by substantially simultaneously transmitting four ultrasonic beams (multi-beam transmission) at different frequencies from one another, and generating ultrasonic images based on the ultrasonic image information. The ultrasonic observation method is used in the ultrasonic observation apparatus shown in FIGS. 1-5.

First, the operator operates the console 11 shown in FIG. 1 to input a command to start ultrasonic observation in a multi-beam transmission mode at different frequencies. In response thereto, the control unit 12 outputs control signals representing the start of operation to the transmission beam setting unit 14, the transmission timing setting unit 15 and the reception control unit 17. The number of ultrasonic beam to be substantially simultaneously transmitted can be selected when the operator inputs the mode information. In the embodiment, four ultrasonic beams are substantially simultaneously transmitted.

The transmission beam setting unit 14 reads out the following information corresponding to the multi-beam transmission mode at different frequencies according to the control signal outputted form the control unit 12.

Beam 1 (TB1): frequency of 4 MHz, aperture width of 6.4 mm, focal distance of 8 cm, image area equal to or more than 6 cm Beam 2 (TB2): frequency of 7.5 MHz, aperture width of 4.8 mm, focal distance of 4 cm, image area equal to or more than 3 cm and less than 6 cm Beam 3 (TB3): frequency of 12 MHz, aperture width of 3.2 mm, focal distance of 2 cm, image area equal to or more than 1am and less than 3 cm Beam 4 (TB4): frequency of 20 MHz, aperture width of 2.4 mm, focal distance of 0.5 cm, image area less than 1 cm The frequencies of ultrasonic beams may be automatically set according to the number of ultrasonic beams as in the embodiment, or manually inputted by the operator. Further, the operator may modify the frequencies that have been automatically set.

Furthermore, the transmission beam setting unit 14 sets the angular interval between ultrasonic beams adjacently transmitted to 90° (=360°/4), and sets initial transmission positions PT0, PT90, PT180, and PT 270 of the four ultrasonic beams. Although the angular interval between ultrasonic beams can be changed by the operator inputting a command, the angular intervals are desirably made as wide as possible in order to avoid crosstalk between ultrasonic beams. Accordingly, in the ultrasonic observation apparatus shown in FIG. 1, the angular interval is initially set to 360°/(number of ultrasonic beams).

Further, the transmission timing setting unit 15 sets PRF based on the lowest frequency (4 MHz) among the above four frequencies. Here, the reason why the lowest frequency is used as reference when PRF is set is that the information on the deeper part of the object can be acquired as the frequency is lower, and therefore, more time is required for the ultrasonic beam to travel to and from the deeper part.

Figure 6:
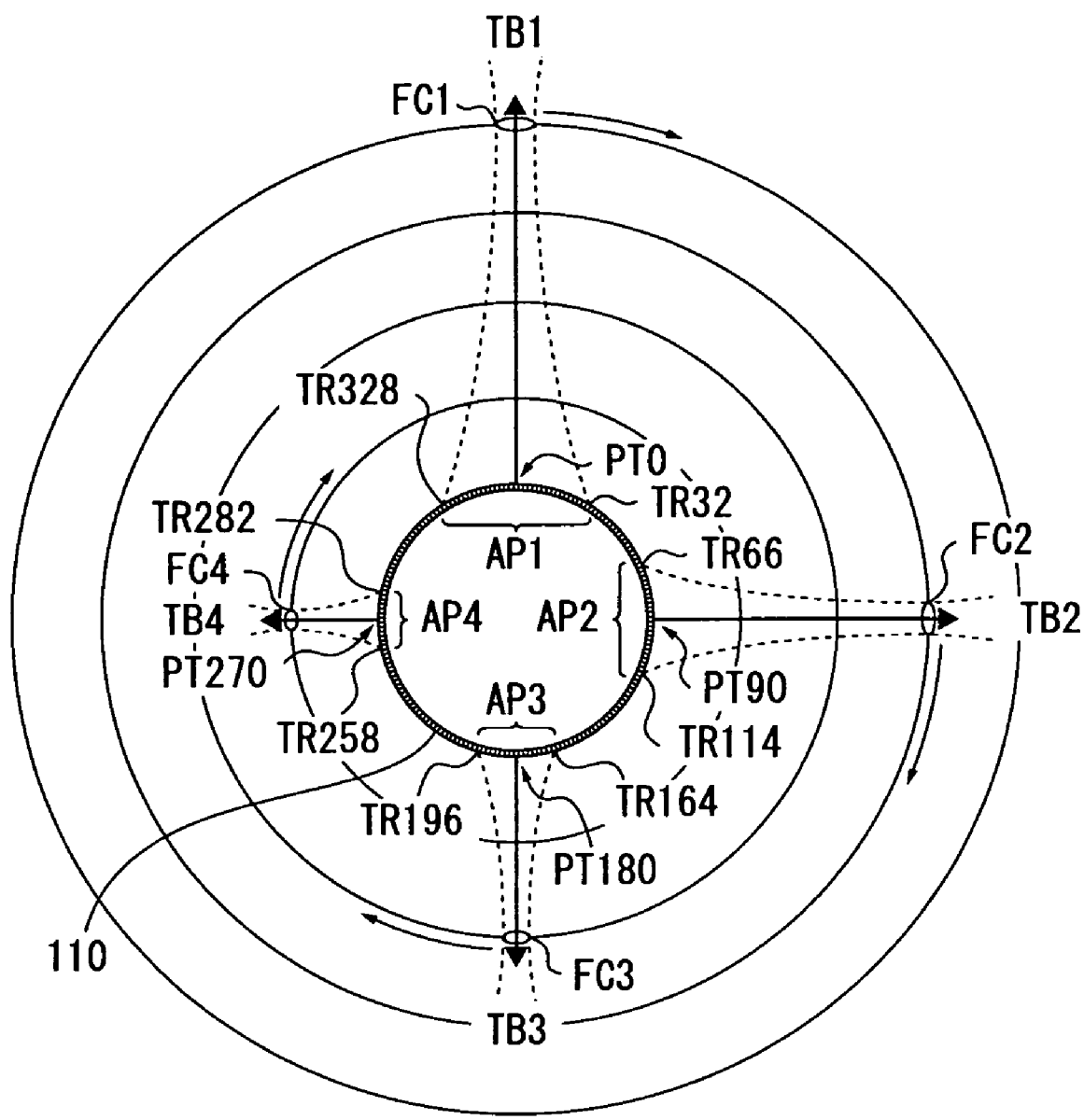
FIG. 6 is a diagram for explanation of an ultrasonic observation method according to the first embodiment of the present invention.

As shown in FIG. 6, the transmission aperture setting part 161 of the drive signal setting unit 16 sets ultrasonic transducers TR328 to TR32 included in the range with a center of the position PT0 and aperture width of 6.4 mm as the transmission aperture AP1 for transmitting the ultrasonic beam at 4 MHz. Further, the transmission aperture setting part 161 sets ultrasonic transducers TR66 to TR144 included in the range with a center of the position PT90 and aperture width of 4.8 mm as the transmission aperture AP2 for transmitting the ultrasonic beam at 7.5 MHz. Furthermore, the transmission aperture setting part 161 sets ultrasonic transducers TR164 to TR196 included in the range with a center of the position PT180 and aperture width of 3.2 mm as the transmission aperture AP3 for transmitting the ultrasonic beam at 12 MHz. Moreover, the transmission aperture setting part 161 sets ultrasonic transducers TR258 to TR282 included in the range with a center of the position PT90 and aperture width of 2.4 mm as the transmission aperture AP4 for transmitting the ultrasonic beam at 20 MHz.

Further, on thus set transmission apertures, the transmission focus setting part 162 performs transmission focus setting such that focal points are formed at predetermined depths for the respective transmission apertures, and the transmission frequency setting part 163 sets frequencies of the drive signal groups to be provided to the respective transmission apertures.

On the other hand, the respective parts of the reception control unit 17 perform setting of the corresponding plural reception apertures, reception focuses, reception frequency bands, and image areas based on the transmission apertures AP1 to AP4.

Referring to FIGS. 1 and 6 again, when the drive signal generating unit 18 generates drive signals according to the setting in the drive signal setting unit 16, ultrasonic beams TB1 to TB4 having different frequencies from one another are transmitted from the transmission apertures AP1 to AP4. The transmitted ultrasonic beams TB1 to TB4 are reflected from certain points within the object, and thereby generated ultrasonic echoes are received by the ultrasonic transducers TR1 to TR360.

Such operation of transmitting and receiving ultrasonic beams is repeated while shifting the positions of the transmission apertures AP1 to AP4 at the PRF set in the transmission timing setting unit 15. For example, in FIG. 6, when the positions of the transmission apertures AP1 to AP4 are shifted by one ultrasonic transducer such that the ultrasonic transducers TR329 to TR33 are used as the transmission aperture AP1, the transmission directions of the ultrasonic beams change by 1°. Thus, an angle range of 360° around the ultrasonic transducer unit 110 is scanned by the respective ultrasonic beams TB1 to TB4.

When receiving the ultrasonic echoes, the ultrasonic transducers TR1 to TR360 output reception signals to the corresponding channels of the reception signal processing unit 20 shown in FIG. 5. In the respective channels, the reception signals are preamplified and converted into digital data (reception data).

Among these reception data, four pieces of reception data outputted from the ultrasonic transducers included in the reception apertures corresponding to the transmission apertures AP1, AP2, AP3 and AP4 (FIG. 6) are selected by the reception data selection part 210 and inputted to the reception focus processing parts 211, 212, 213 and 241, respectively. That is, the reception data corresponding to the ultrasonic beam at 4 MHz is inputted to the data processing system 211-214, the reception data corresponding to the ultrasonic beam at 7.2 MHz is inputted to the data processing system 221-224, the reception data corresponding to the ultrasonic beam at 12 MHz is inputted to the data processing system 231-234, and the reception data corresponding to the ultrasonic beam at 20 MHz is inputted to the data processing system 241-244.

In each of the data processing systems, delay addition processing, reception filter processing, and gain/gradation processing are performed on the reception data under the control of the reception control unit 17. Thereby, four kinds of B-mode image data by frequency are acquired from the sound ray data processing unit 21. The four kinds of B-mode image data are subjected to conversion processing of scan formats in the B-mode image data generating unit 22 to be converted into B-mode image data for display.

FIG. 7 shows image areas set by the image region setting part 174 according to focal depths of the ultrasonic beams from the ultrasonic transducer unit 110. As shown in FIG. 7, the depth region equal to or more than 6 cm is set for the ultrasonic beam at focal depth of 8 cm (frequency of 4 MHz). Further, the depth region equal to or more than 3 cm and less than 6 cm is set for the ultrasonic beam at focal depth of 4 cm (frequency of 7.5 MHz). Furthermore, the depth region equal to or more than 1 cm and less than 3 cm is set for the ultrasonic beam at focal depth of 2 cm (frequency of 12 MHz). Further, the depth region less than 1 cm is set for the ultrasonic beam at focal depth of 0.5 cm (frequency of 20 MHz).

Figure 8:
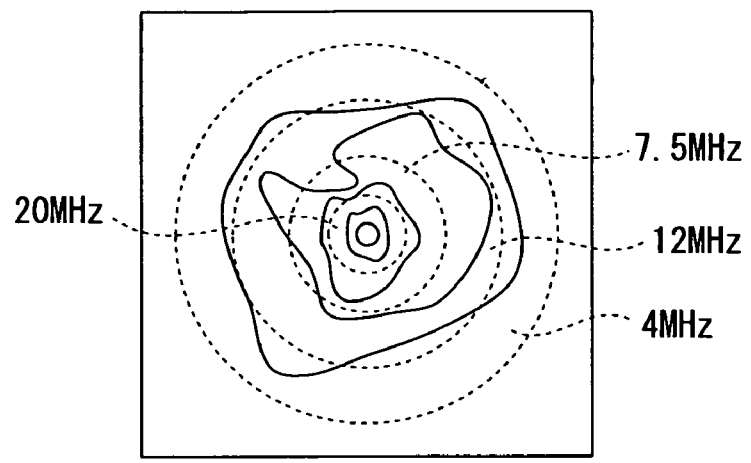
FIG. 8 is a schematic diagram showing an example of a synthesized image generated by an image synthesizing unit shown in FIG. 1.

As shown in FIG. 8, the image synthesizing unit 23 extracts image areas from the four kinds of B-mode image data by frequency (4 MHz, 7.5 MHz, 12 MHz and 20 MHz), and performs processing of synthesizing those.

Thus generated B-mode image data by frequency and synthesized image data are processed according to the setting in the display format setting unit 27, further subjected to necessary image processing in the image processing unit 25, and then, outputted to the display unit 26. Thereby, ultrasonic images are displayed in a display format desired by the user.

Figure 9:
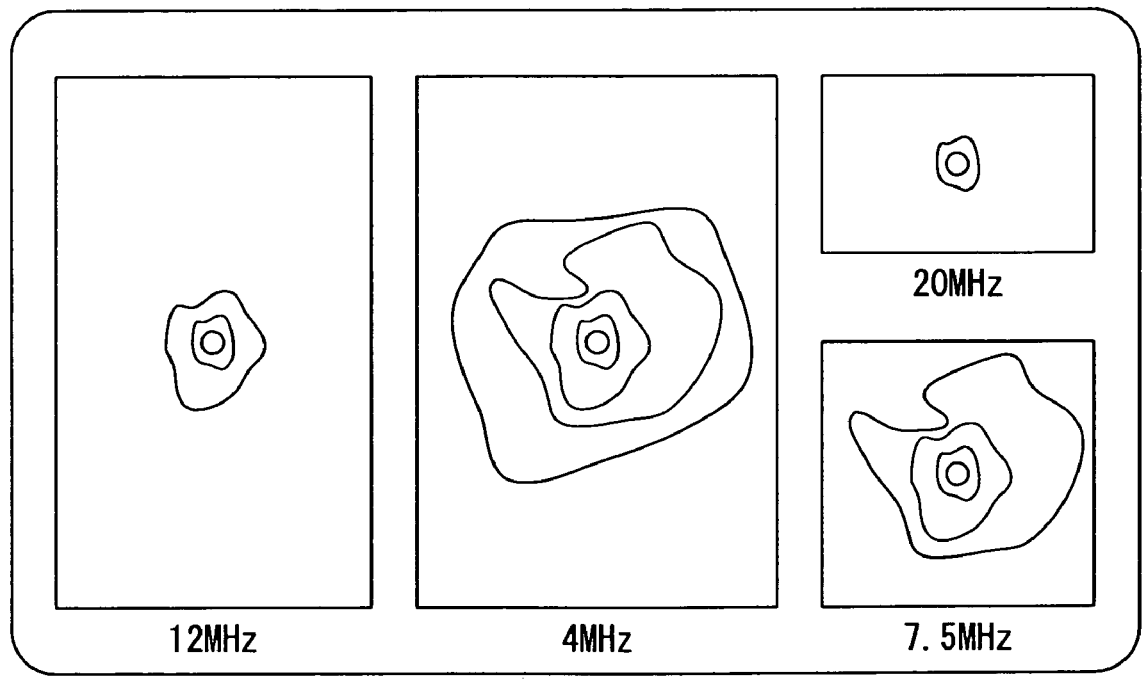
FIG. 9 is a schematic diagram showing an example of an image display format set by a display format setting unit as shown in FIG. 1.
Figure 10:
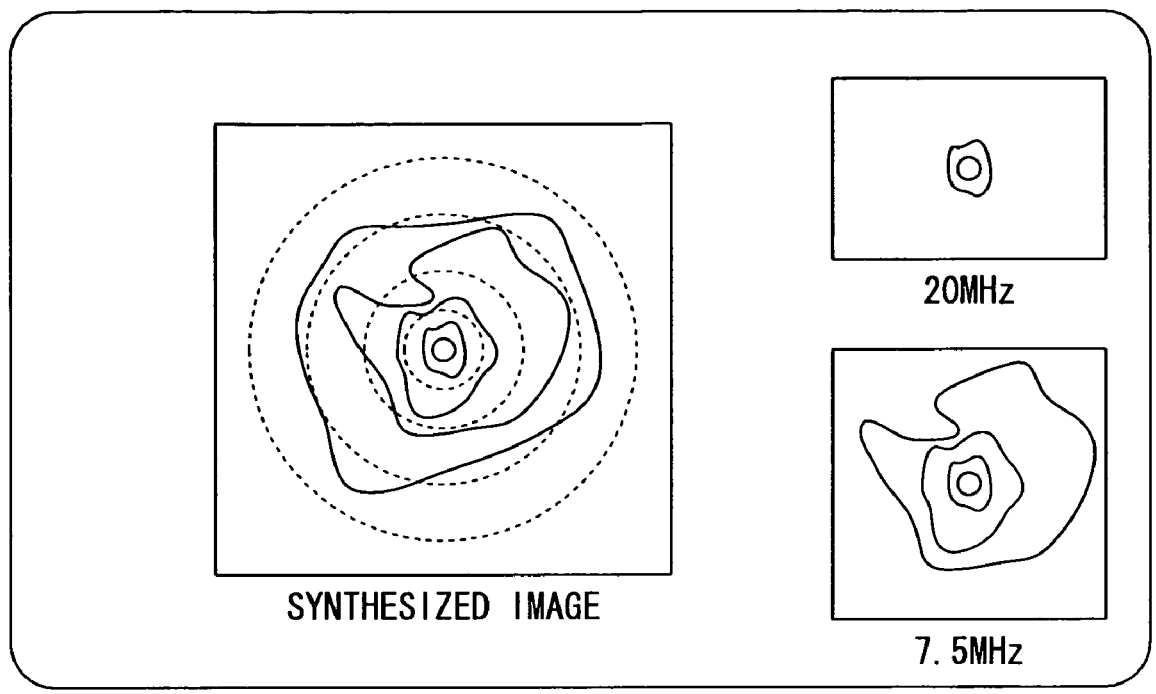
FIG. 10 is a schematic diagram showing another example of an image display format set in the display format setting unit as shown in FIG. 1.

As a display format set in the display format setting unit 27, for example, one can be selected from the following formats.
(1) Display format for displaying a synthesized image only (FIG. 8).
(2) Display format for displaying images by frequency only (FIG. 9).
   In this case, the number of B-mode images (e.g., one to four), kinds (4 MHz, 7.5 MHz, 12 MHz and 20 MHz), sizes, and the layouts in the screen can be selected.
(3) Display format for displaying both a synthesized image and images by frequency (FIG. 10).
   In this case, the number of B-mode images, kinds, sizes, and the layouts in the screen can be selected.

As explained above, according to the embodiment, since the radial scan is performed by multi-beam, plural kinds of ultrasonic images obtained by transmitting ultrasonic beams having different frequencies can be acquired without reducing the frame rate compared to the case of using a single beam. Further, in the embodiment, since the frequencies are set with respect to the plural transmission apertures, and filter processing corresponding to the transmission frequencies is performed on the signals received in the reception apertures corresponding to the transmission apertures, unlike the method of transmitting a wideband ultrasonic beam and separating frequency bands at the time of reception, great transmission power can be obtained and the S/N ratio can be improved.

Furthermore, in the embodiment, since the high resolving power in the shallow part and the penetration depth of the beams to the deep part are compatible by synthesizing plural ultrasonic images obtained by transmitting ultrasonic beams having different frequencies from one another based on the respective focal depths, imaging can be performed in a broad area from the shallow part to the deep part in a good condition. In such images, since gradation correction processing has been performed according to the transmission frequencies with respect to plural image areas, there is no unnaturalness between different image areas and the images become easily viewable overall. Therefore, in medical diagnoses, appropriate judgment can be made based on one image.

Furthermore, according to the embodiment, since plural kinds of ultrasonic images obtained by transmitting ultrasonic beams having different frequencies from one another can be acquired without replacing the probe (endoscope) and they can be selected and displayed according to the user's preference, the diagnostic efficiency can be raised in the sites of medical diagnoses.

Although the transmission apertures are simply arranged in the order of ultrasonic beam frequencies in FIG. 6, the arrangement of transmission apertures is desirably determined in consideration of values of the ultrasonic beam frequencies. For example, since the apertures and beam diameters of the ultrasonic beams at 7.5 MHz and 4 MHz are relatively wide, it is desirable that the transmission apertures of those ultrasonic beams are set opposite to each other on the circumference of the ultrasonic transducer unit 110. Thereby, crosstalk between the ultrasonic beams can be suppressed.

Although four ultrasonic beams having different frequencies from one another are substantially simultaneously transmitted in the above-mentioned first embodiment of the present invention, the number of ultrasonic beams and the values of frequencies can be set to various values according to the operator's preferences in the ultrasonic observation apparatus shown in FIG. 1. In the second to sixth embodiments as below, specific examples of frequencies and scan methods of ultrasonic beams will be explained.

An ultrasonic observation method according to the second embodiment of the present invention will be explained by referring to FIGS. 11 to 13. In the embodiment, four ultrasonic beams having the same frequency but different focal depths from one another are substantially simultaneously transmitted.

In this case, the angular interval between adjacent ultrasonic beams is set to 90° (=360°/4), and the transmission apertures, transmission focus, reception apertures, reception focus and image areas are set based on the following information stored in the transmission beam information storage unit 140 (FIG. 1).

Figure 11:
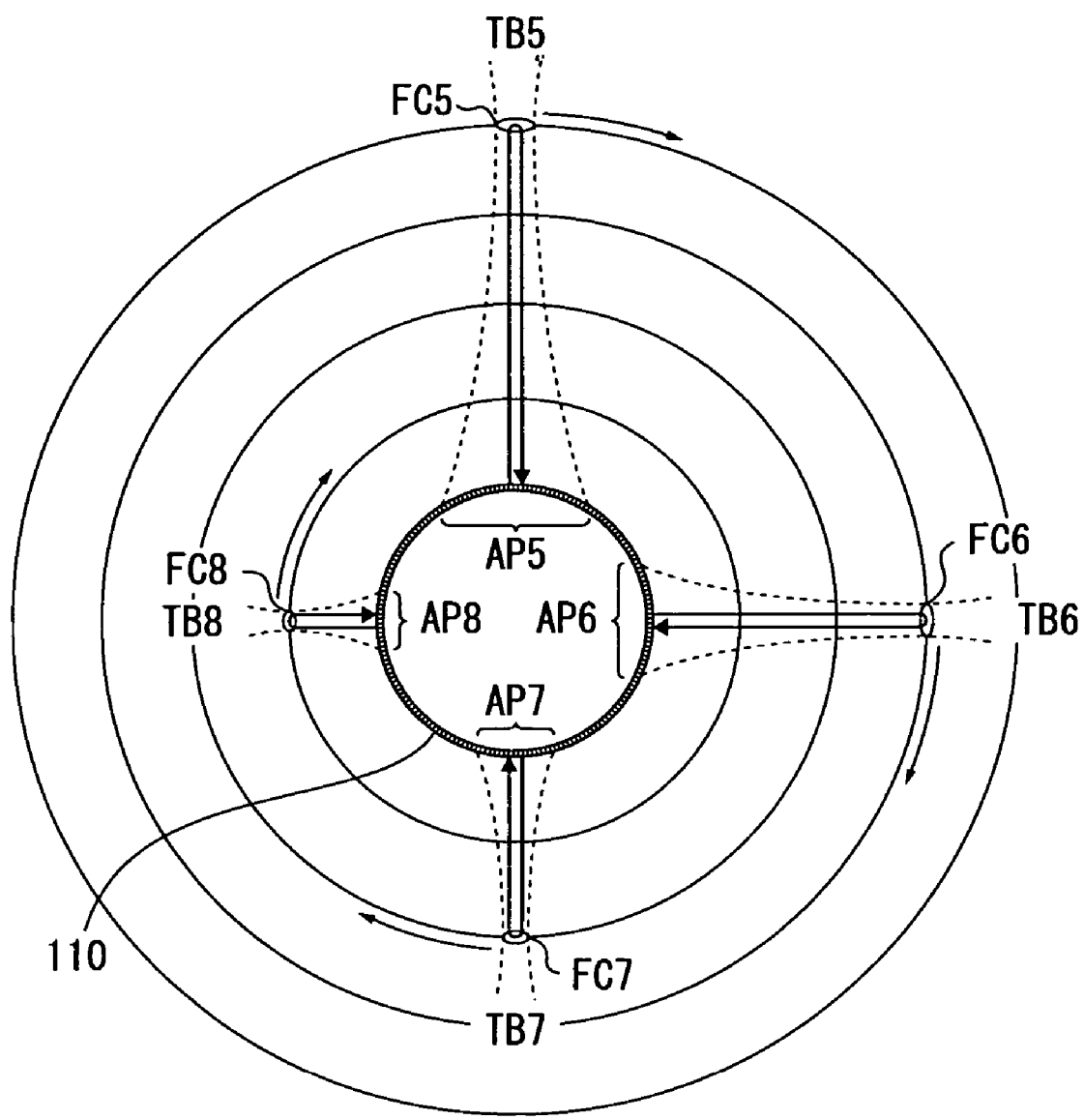
FIG. 11 is a diagram for explanation of an ultrasonic observation method according to the second embodiment of the present invention.
Figure 12:
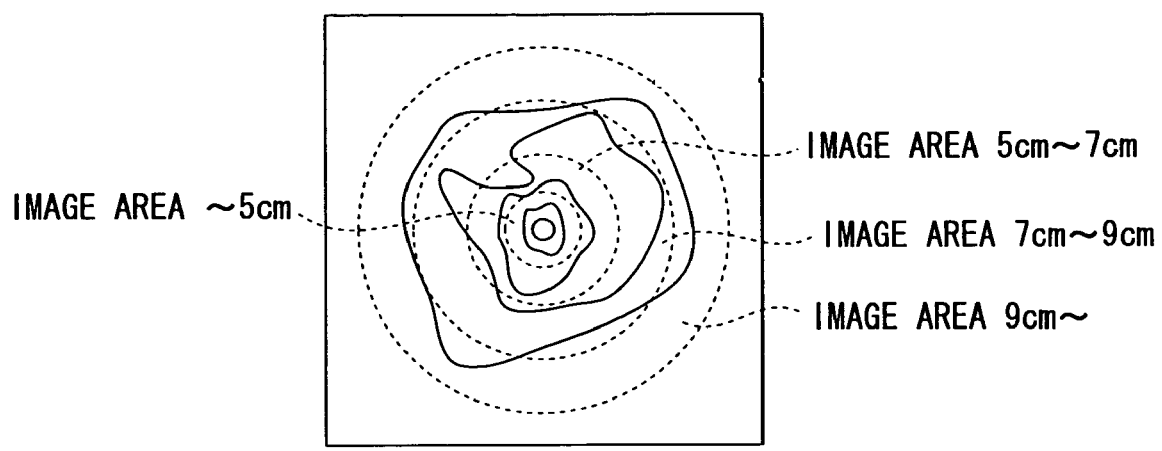
FIG. 12 is a schematic diagram showing an example of a synthesized image generated in the ultrasonic observation method according to the second embodiment of the present invention.

Beam 1 (TB5): frequency of 4 MHz, aperture width of 6.4 mm, focal distance of 10 cm, image area equal to or more than 9 cm, beam diameter of 4.8 mm Beam 2 (TB6): frequency of 4 MHz, aperture width of 6.4 mm, focal distance of 8 cm, image area equal to or more than 7 cm and less than 9 cm, beam diameter of 1.7 mm Beam 3 (TB7): frequency of 4 MHz, aperture width of 6.4 mm, focal distance of 6 cm, image area equal to or more than 5 cm and less than 7 cm, beam diameter of 0.8 mm Beam 4 (TB8): frequency of 4 MHz, aperture width of 6.4 mm, focal distance of 4 cm, image area less than 5 cm, beam diameter of 0.16 mm Thereby, an angle range of 360° around the ultrasonic transducer unit 110 is scanned by the ultrasonic beams TB5 to TB8 respectively transmitted from transmission apertures AP5 to APB shown in FIG. 11.

The reception signals received by reception apertures set correspondingly to the transmission apertures AP5 to APB are subjected to the same processing as has been explained in the first embodiment. Thereby, four kinds of B-mode image data by focal depth are generated.

Furthermore, synthesized image data is generated based on those B-mode image data. FIG. 12 shows a synthesized image represented by the synthesized image data. The synthesized image is formed by extracting the image areas set according to the focal depths from the plural B-mode images and synthesizing them. Here, the image areas set for the respective B-mode images represent regions near the respective focal points of the transmitted and received ultrasonic beams (focal points FC5 to FC8 in FIG. 11), i.e., regions where the beam diameters are the narrowest, resolving power is the highest in the respective B-mode images, and the status of the object is expressed best. Such a synthesized image is of the same quality as an image obtained by normal dynamic focus.

As a display format of the four kinds of B-mode images by focal depth and the synthesized image, similarly to those shown in FIGS. 8 to 10, the operator can select one according to preference from among a display format of the synthesized image only, a display format of the B-mode images by focal depth only (one to four images), and a display format of displaying both the synthesized image and the B-mode images by focal depth. Further, in the case where plural images are displayed, the operator may select the sizes and layouts of the respective images according to preference.

As explained above, according to the embodiment, by transmitting and receiving plural ultrasonic beams at different focal depths, dynamically focused ultrasonic images can be obtained in the same period as that for normal single beam transmission. Therefore, the image quality of ultrasonic images can be improved without reducing the frame rate.

Next, an ultrasonic observation method according to the third embodiment of the present invention will be explained by referring to FIG. 13. In the embodiment, in the case where four ultrasonic beams having the same frequency but different focal depths from one another are substantially simultaneously transmitted, the ultrasonic beams are designed such that the beam diameters become the same at the focal positions.

In the second embodiment of the present invention, when the plural ultrasonic beams are formed, the focal distances are changed only by transmission focus setting without changing the aperture widths. Accordingly, the beam diameter at the focal position is smaller as the focal distance is shorter, and the beam diameter at the focal position is larger as the focal distance is longer (near the periphery in FIG. 12). Therefore, in the synthesized image shown in FIG. 12, the resolving power near the center is high, and gradually becomes lower toward the outer side. Contrary, in the embodiment, the beam diameters are the same in order to obtain nearly equal resolving power in the entire synthesized image.

In this case, the transmission apertures, transmission focus, reception apertures, reception focus and image areas are set based on the following information stored in the transmission beam information storage unit 140 (FIG. 1).

Figure 13:
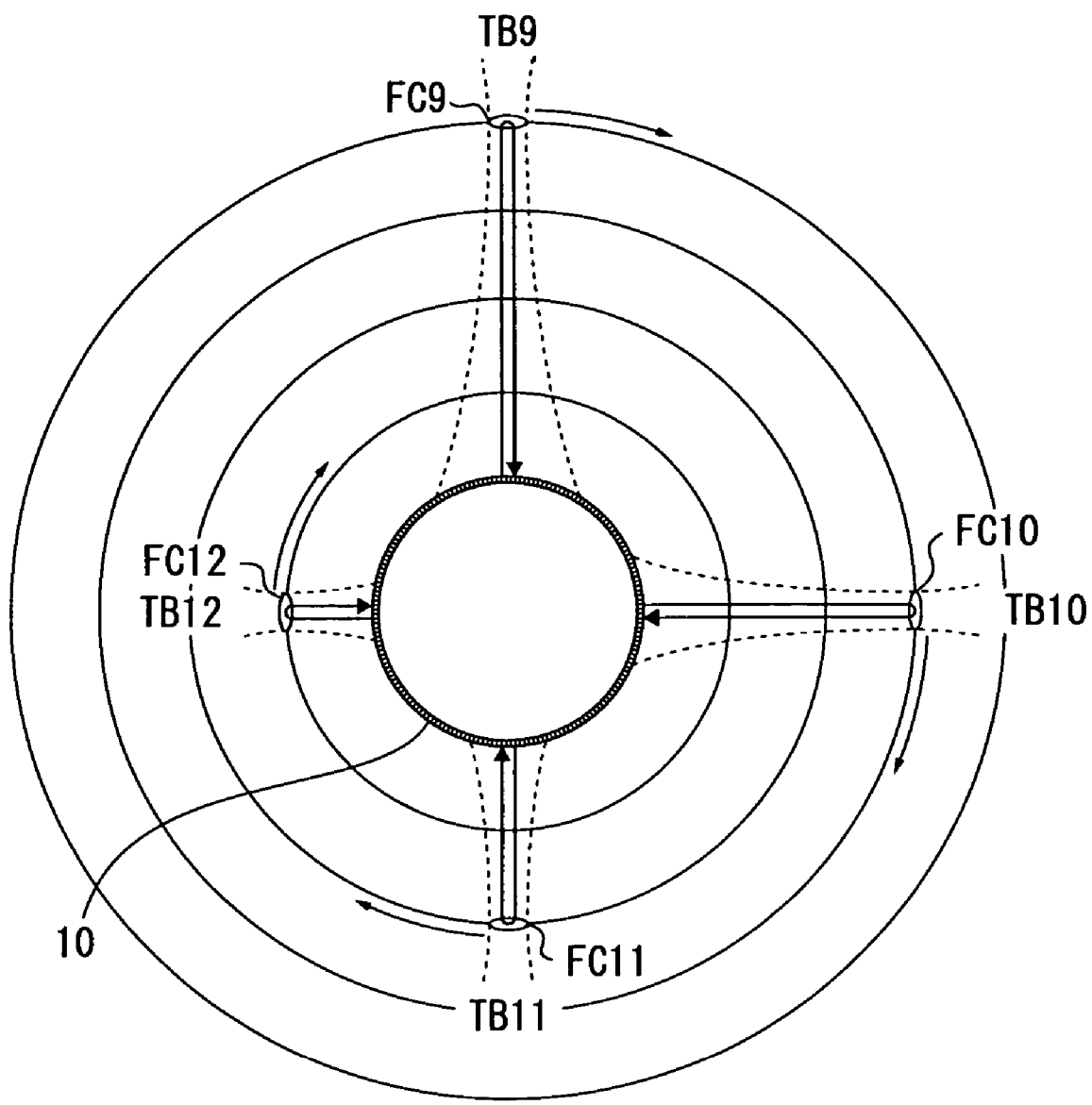
FIG. 13 is a diagram for explanation of an ultrasonic observation method according to the third embodiment of the present invention.

Beam 1 (TB9): frequency of 4 MHz, aperture width of 8 mm, focal distance of 10 cm, image area equal to or more than 9 cm, beam diameter of 4.8 mm Beam 2 (TB10): frequency of 4 MHz, aperture width of 6.4 mm, focal distance of 8 cm, image area equal to or more than 7 cm and less than 9 cm, beam diameter of 1.7 mm Beam 3 (TB11): frequency of 4 MHz, aperture width of 6.4 mm, focal distance of 6 cm, image area equal to or more than 5 cm and less than 7 cm, beam diameter of 0.8 mm Beam 4 (TB8): frequency of 4 MHz, aperture width of 4.3 mm, focal distance of 4 cm, image area less than 5 cm, beam diameter of 0.16 mm Thereby, as shown in FIG. 13, an angle range of 360° around the ultrasonic transducer unit 110 is scanned by the four ultrasonic beams having nearly equal beam diameters at the focal points FC9 to FC12. The subsequent processing on the reception signals is the same as that in the third embodiment.

Thus, according to the embodiment, the resolving power in the synthesized image can be made nearly constant regardless of depths, which correspond to image areas in the synthesized image.

Next, an ultrasonic observation method according to the fourth embodiment of the present invention will be explained by referring to FIGS. 14A and 14B. In the embodiment, plural ultrasonic beams having the same frequency and the same focal depth are substantially simultaneously transmitted.

Figure 14A:
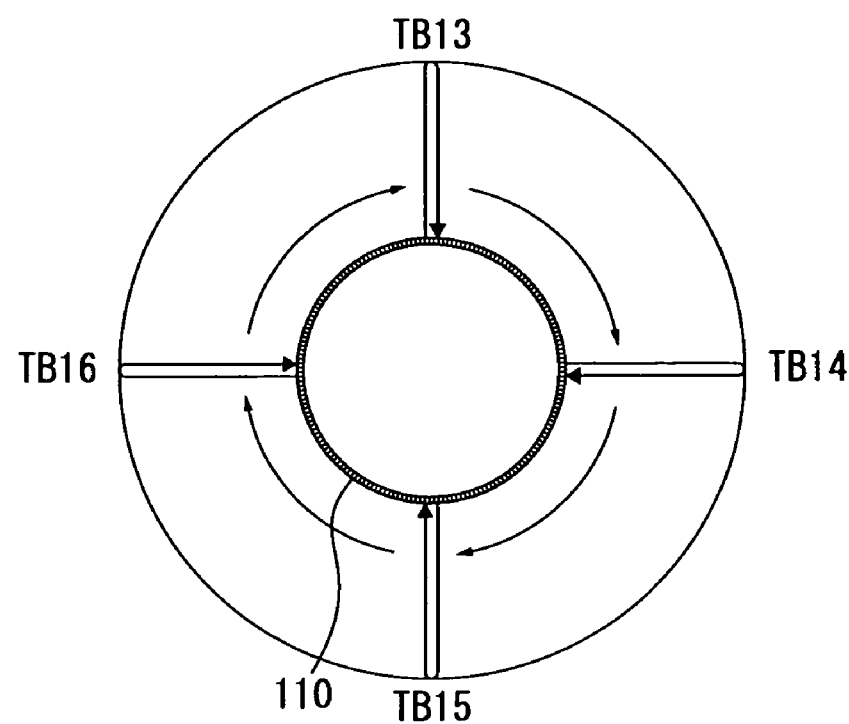
FIGS. 14A and 14B are diagrams for explanation of an ultrasonic observation method according to the fourth embodiment of the present invention.
Figure 14B:
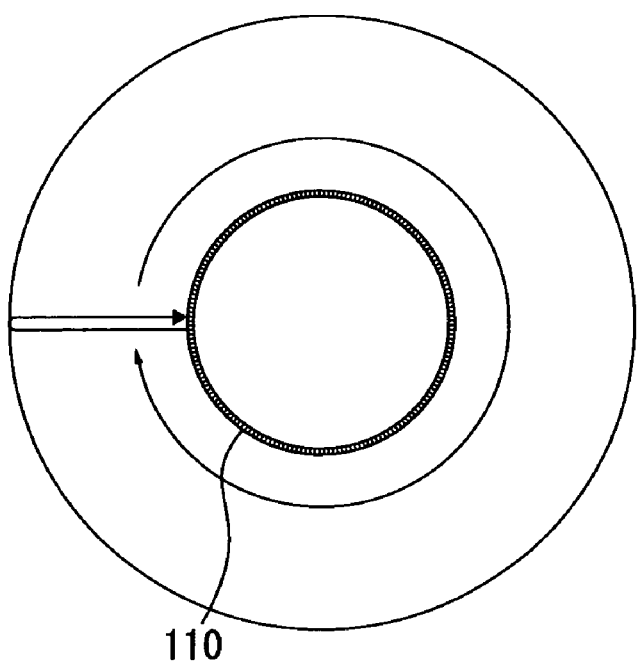

For example, as shown in FIG. 14A, total ultrasonic image information about an angle range of 360° around the ultrasonic transducer unit 110 can be acquired by rotating transmission directions of four ultrasonic beams TB13 to TB16 separated by 90° from one another. On the other hand, FIG. 14B shows an example of rotating the transmission direction of one ultrasonic beam by 360°. As clearly found by comparison between FIGS. 14A and 14B, according to the embodiment, the frame rate is made fourfold while keeping the resolving power nearly equal to that in the case of single-beam transmission (FIG. 14B).

Next, an ultrasonic observation method according to the fifth embodiment of the present invention will be explained by referring to FIG. 15. In the embodiment, an angle range of 360° around the ultrasonic transducer unit 110 is divided into plural regions and the plural regions are scanned by respective ultrasonic beams having different frequencies from one another.

In the case where four ultrasonic beams are transmitted, the angular interval between adjacent ultrasonic beams is set to 90° (=360°/4), and the transmission apertures, transmission focus, reception apertures, reception focus and image areas are set based on the following information stored in the transmission beam information storage unit 140 (FIG. 1).

Beam 1 (TB17): frequency of 20 MHz, aperture width of 2.4 mm, focal distance of 0.5 cm, scan range equal to or more than 45° and less than 125° (region A)

Beam 2 (TB18): frequency of 12 MHz, aperture width of 3.2 mm, focal distance of 2 cm, scan range equal to or more than 125° and less than 225° (region B)

Beam 3 (TB19): frequency of 7.5 MHz, aperture width of 4.8 mm, focal distance of 4 cm, scan range equal to or more than 225° and less than 315° (region C)

Beam 4 (TB20): frequency of 4 MHz, aperture width of 6.4 mm, focal distance of 8 cm, scan range equal to or more than 3150 and less than 405° (45°) (region D)

Figure 15:
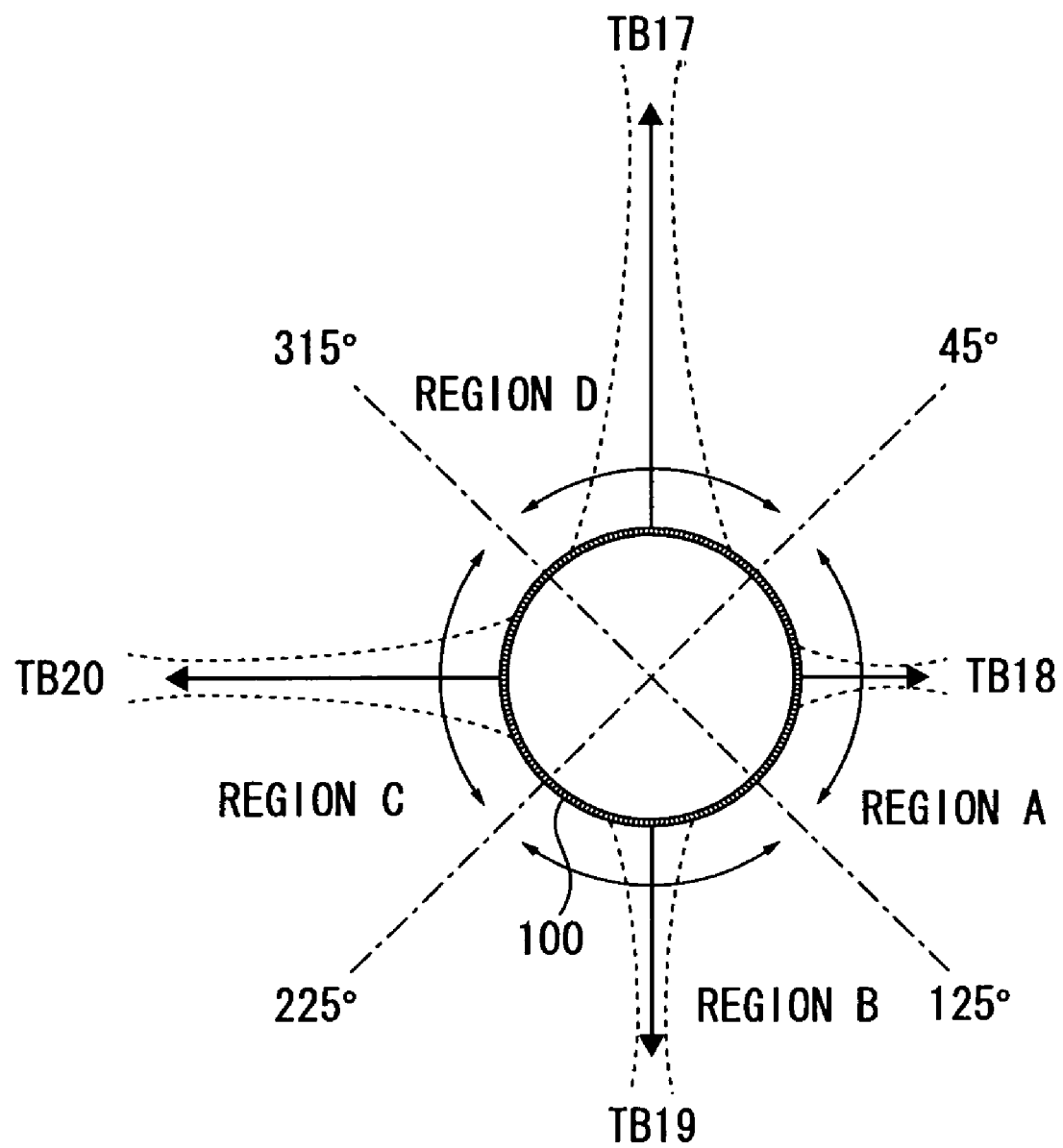
FIG. 15 is a diagram for explanation of an ultrasonic observation method according to the fifth embodiment of the present invention.

Thereby, as shown in FIG. 15, the regions A to D are scanned by the ultrasonic beams TB17 to TB20 having different frequencies from one another.

According to the embodiment, ultrasonic images in which desired ranges are expressed with high resolving power can be obtained at the nearly equal frame rate and scan density to those in the case of scanning an angle range of 360° by a single beam. Therefore, such an ultrasonic observation method is effective in the case where the depth of a part desired to be observed is known as to the particular part.

Although the ranges of regions A to D are set such that the respective scan regions are equal in the embodiment, the respective scan regions may be changes automatically or manually according to the range of the part to be observed.

Next, an ultrasonic observation method according to the sixth embodiment of the present invention will be explained by referring to FIGS. 16-17B.

Here, in the case where plural ultrasonic beams having different frequencies from one another are substantially simultaneously transmitted, an ultrasonic beam having a lower frequency can reach the deeper part of the object compared to an ultrasonic beam having a higher frequency, and therefore, time is required for one transmission and reception. Accordingly, when the PRF of the ultrasonic beam having a higher frequency is made higher, the entire transmission and reception efficiency can be improved. However, if the PRFs are set simply with respect to the frequencies, the angular interval between plural ultrasonic beams gradually shifts from the initial setting (e.g., 90° for four beams) and becomes narrower, and crosstalk is caused. Accordingly, in the embodiment, besides PRFs of plural ultrasonic beams are set with respect to the frequencies, some efforts are made for the order of the transmission and reception directions.

Figure 16:
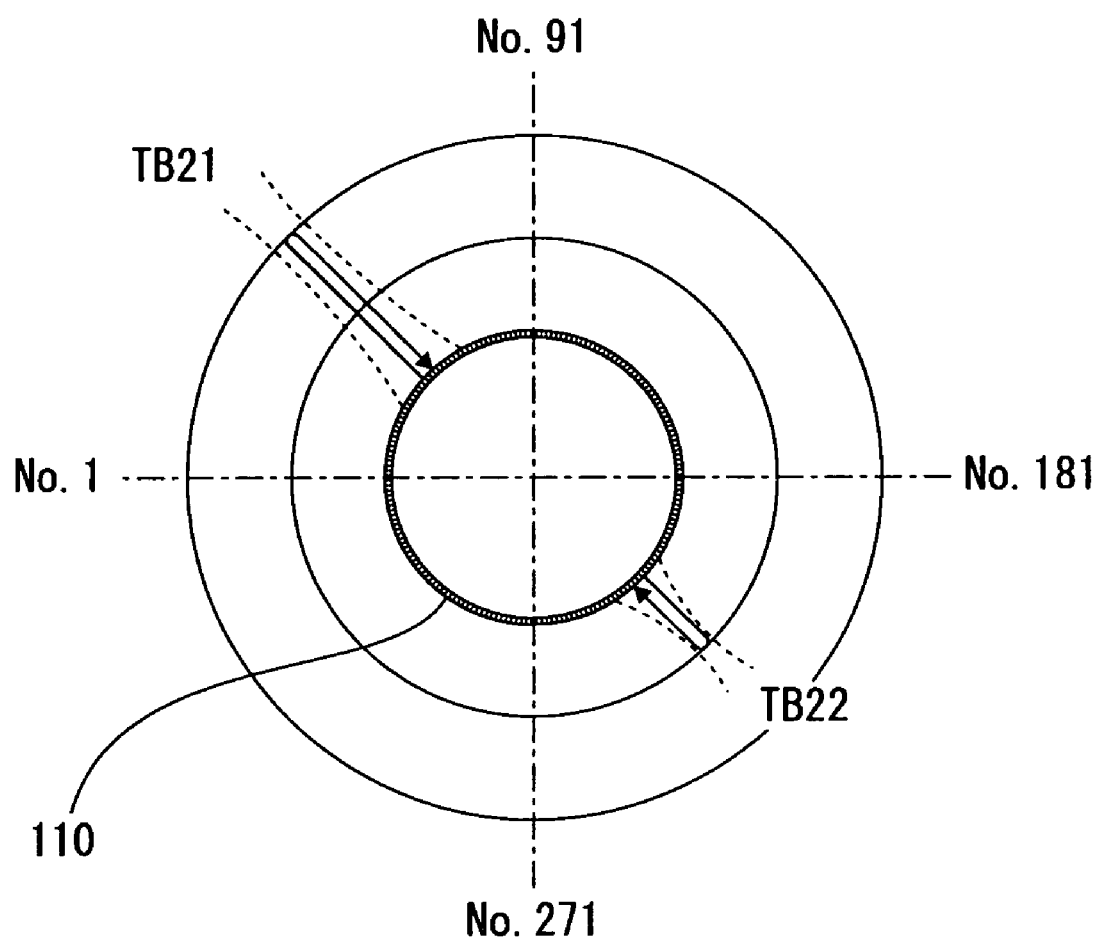
FIG. 16 is a diagram for explanation of an ultrasonic observation method according to the sixth embodiment of the present invention.
Figure 17A:
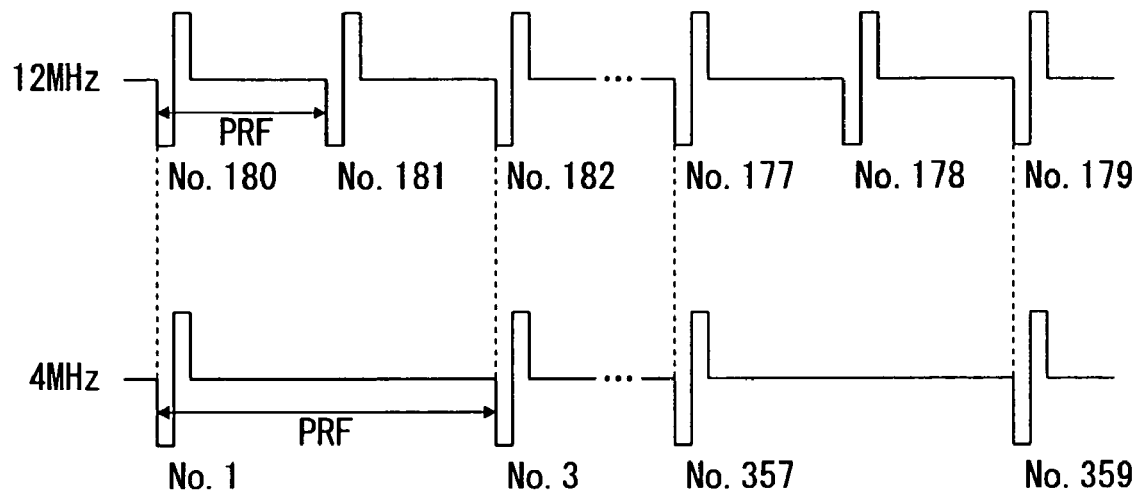
FIGS. 17A and 17B are pulse generation timing charts to be used in the ultrasonic observation method according to the sixth embodiment of the present invention.

Hereinafter, for simplicity, as shown in FIG. 16, the case where two kinds of an ultrasonic beam TB21 at 4 MHz and an ultrasonic beam TB22 at 12 MHz are substantially simultaneously transmitted will be explained. FIGS. 17A and 17B are pulse generation timing charts for transmitting the ultrasonic beam TB21 and the ultrasonic beam TB22. In the embodiment, the sound ray density for one frame is set to 360 (scan interval 1°), and "No. 1" to "No. 360" in FIGS. 16-17B indicate transmission and reception directions of the ultrasonic beams (sound ray directions).

First, as shown in FIG. 16, the first scan is performed as to an angle range of 360° around the ultrasonic transducer unit 110 by the ultrasonic beam TB21 and the ultrasonic beam TB22. In this regard, as shown in FIG. 17A, the ultrasonic beam TB21 at 4 MHz is set to start scanning from the sound ray direction "No. 1" with the angular interval of 20 and a pulse repetition period of 0.2 msec where the pulse repetition period represents a reciprocal number of the PRF. On the other hand, the ultrasonic beam TB22 at 12 MHz is set to start scanning from the sound ray direction "No. 180" with the angular interval of 1° and the pulse repetition period of 0.1 msec. That is, while the ultrasonic beam TB21 makes one round trip, the ultrasonic beam TB22 makes two round trips. Thus, by setting the PRF and sound ray density of the ultrasonic beam TB22 to be twice the PRF and sound ray density of the ultrasonic beam TB21, the angular interval between the two ultrasonic beams TB21 and TB22 can be kept nearly at 180°.

Figure 17B:
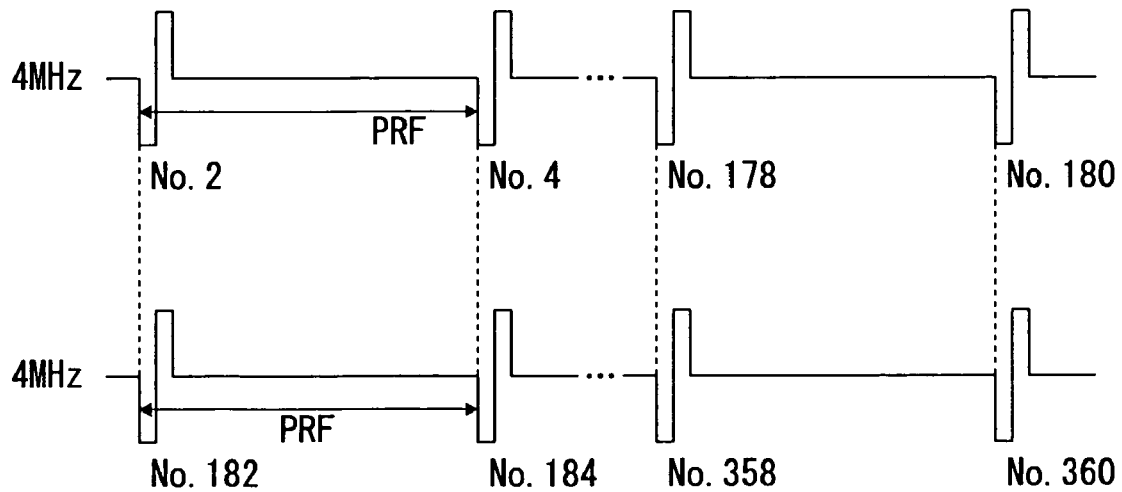

Next, as shown in FIG. 17B, the second scan is performed by two ultrasonic beams at 4 MHz. In the second scan, the ultrasonic beams are transmitted and received as to the sound ray directions that are not scanned in the first scan. That is, two ultrasonic beams are set with the angular interval of 2° and the pulse repetition period of 0.2 msec, such that one ultrasonic beam starts scanning from the sound ray direction "No. 2" and the other ultrasonic beam starts scanning from the sound ray direction "No. 182".

By such two scans, two kinds of ultrasonic image information on ultrasonic beams at 4 MHz and 12 MHz are acquired. The ultrasonic image information is processed in the same way as has been explained in the first embodiment of the present invention. Consequently, B-mode images by frequency and a synthesized image thereof are generated.

Here, in comparison to the case where the ultrasonic beams at 4 MHz and 12 MHz are transmitted and received at scan angular interval of 1° and the equal PRF, the time taken for the first scan is ½ and the time taken for the second scan is ¼, and the total time is ¾.

Since an angle range of 360° around the ultrasonic transducer unit 110 has been once scanned by the first scan, ultrasonic images can be generated thereby. Although the transmission of the ultrasonic beam at 4 MHz has been skipped and the sound ray density becomes rough, the beam diameter of the ultrasonic beam at a low frequency is large and the scan region is nearly entirely covered.

As explained above, according to the embodiment, the frame rate as a whole can be improved while preventing generation of crosstalk without reducing resolving power by maintaining the relative position of the substantially simultaneously transmitted ultrasonic beams.

In the above-mentioned first to sixth embodiments, frequencies of the reception signals corresponding to frequencies of the transmitted ultrasonic beams (basic frequency components) are extracted in the reception filter processing parts 212 to 242 shown in FIG. 5. However, harmonic imaging may be performed by extracting higher harmonic waves having frequency components of an integral multiple (e.g., twice) of basic frequency components. In the case, the reception frequency setting part 173 sets the frequency of the reception filter processing part 212 based on the setting value of the transmission frequency setting part 163 under the control of the control unit 12.

Next, an ultrasonic observation apparatus according to the seventh embodiment of the present invention will be explained by referring to FIGS. 18 and 19.

Figure 18:
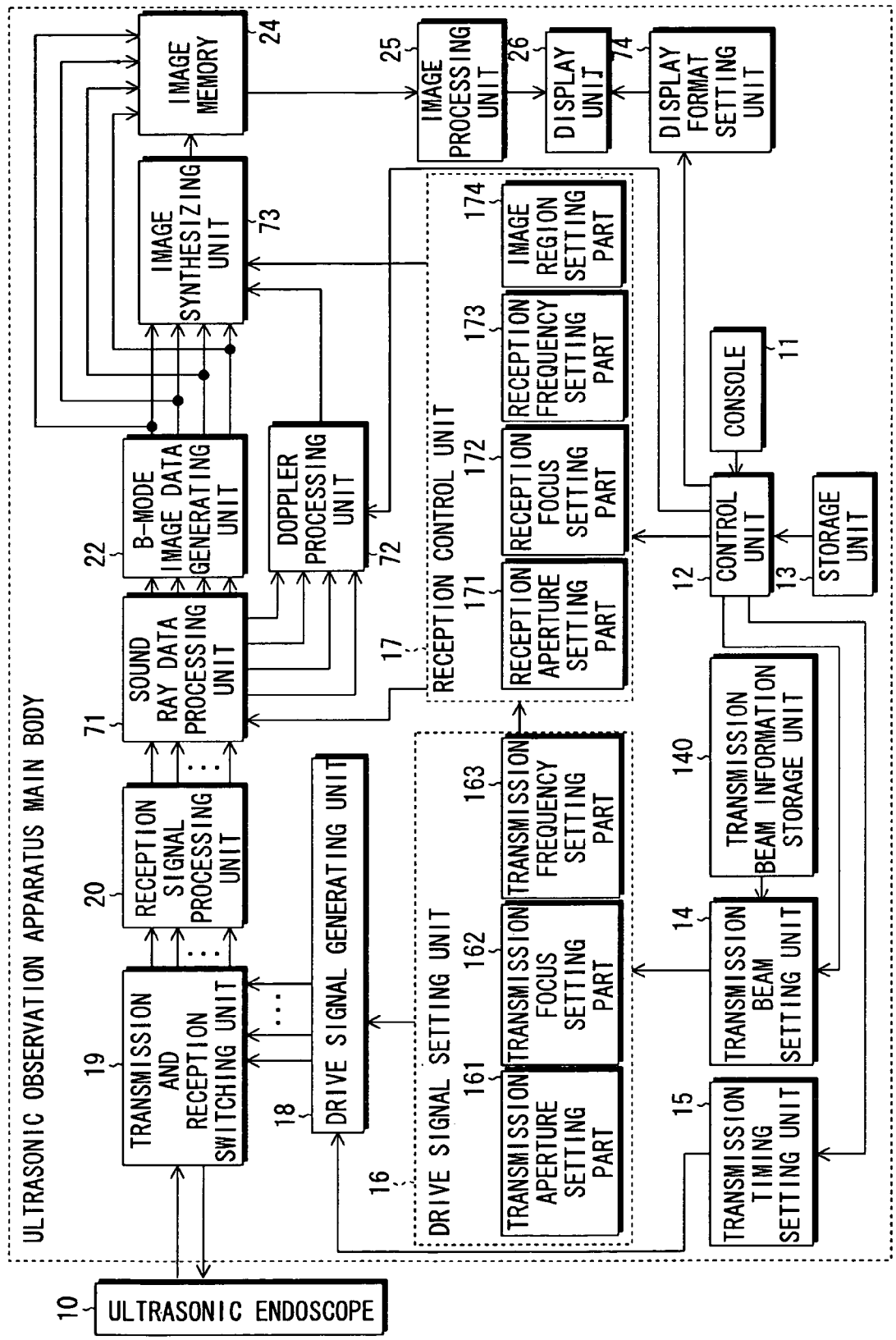
FIG. 18 is a block diagram showing a constitution of an ultrasonic observation apparatus according to the seventh embodiment of the present invention.

As shown in FIG. 18, the ultrasonic observation apparatus according to the embodiment has a sound ray data processing unit 71, an image synthesizing unit 73, a display format setting unit 74 as shown in FIG. 18 in place of the sound ray data processing unit 21, the image synthesizing unit 23, the display format setting unit 27 shown in FIG. 1, and further has a Doppler processing unit 72. Other constitution is the same as that of the ultrasonic observation apparatus shown in FIG. 1.

Figure 19:
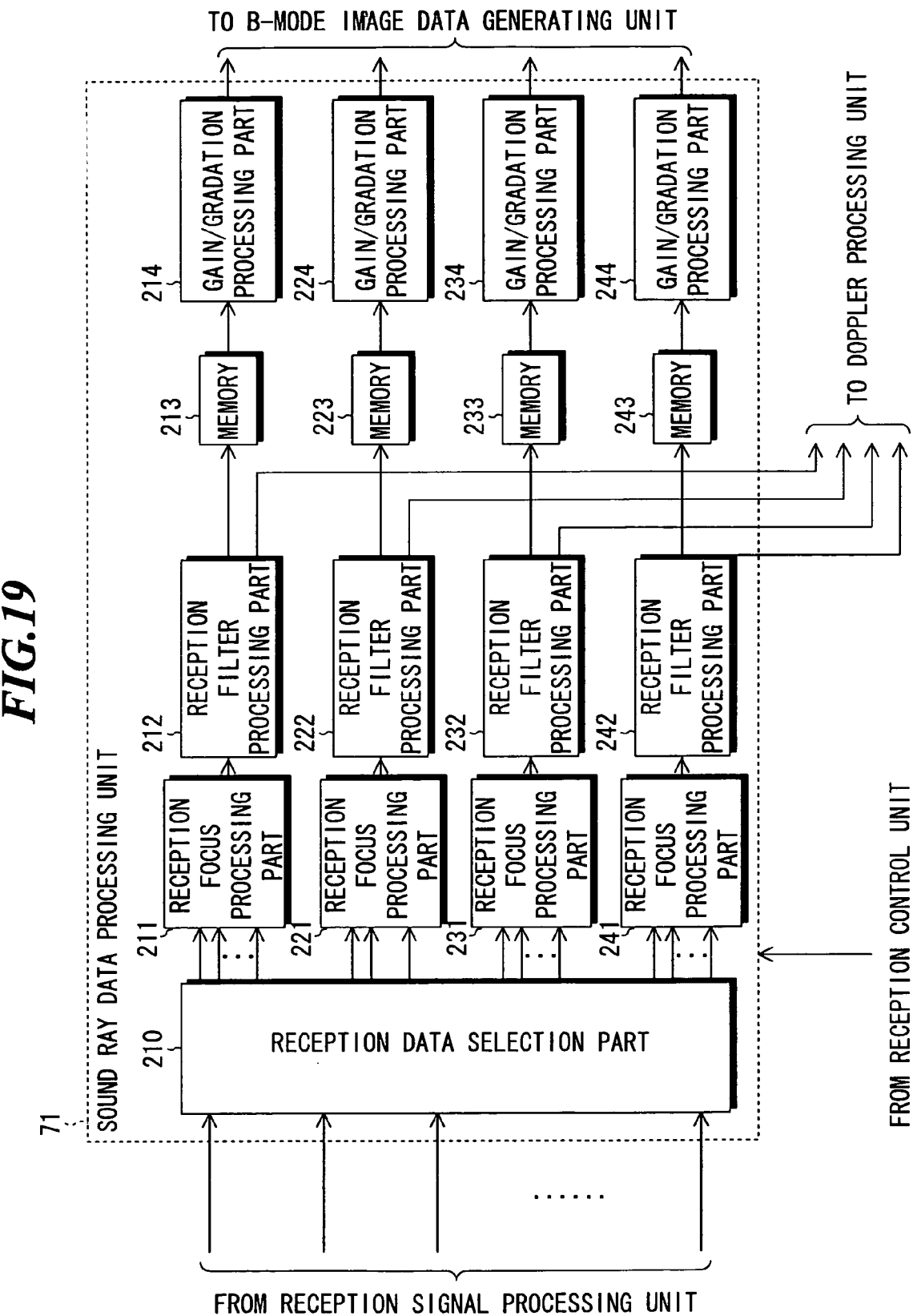
FIG. 19 is a block diagram showing a constitution of a sound ray data processing unit shown in FIG. 18.

FIG. 19 is a block diagram showing a constitution of the sound ray data processing unit 71. The sound ray data processing unit 71 includes the reception data selection part 210 and plural data processing systems 211-214, 221-224, 231-234 and 241-244 provided according to the number of ultrasonic beams to be transmitted similarly to the sound ray data processing unit 21 shown in FIG. 5. The sound ray data generated in the reception filter processing parts 212-242 are once stored in the memories 213-243 in order to generate B-mode images, and inputted to the Doppler processing unit 72 for generating Doppler images.

Referring to FIG. 18 again, the Doppler processing unit 72 removes high frequency components from the reception signals that have been subjected to reception focus processing based on the sound ray data outputted from the sound ray data processing unit 71, and performs orthogonal phase detection processing on the reception signals. Furthermore, the Doppler processing unit 72 removes unwanted clutter components produced by the variations in specular echoes of vessel walls, heart walls and so on from the reception signals that have been subjected to the orthogonal phase detection processing. Thus, Doppler image data formed by extracting only the reflection components from blood stream is generated. The Doppler image data is outputted to the image synthesizing unit 73.

The image synthesizing unit 73 generates synthesized B-mode image data representing a synthesized B-mode image formed by synthesizing plural B-mode images based on plural kinds of B-mode image data generated in the B-mode image data generating unit 22, and generates synthesized image data representing a synthesized image of one of the B-mode images or the synthesized B-mode image and the Doppler image. In the synthesized image, the B-mode image or the synthesized B-mode image may be expressed by brightness and the Doppler images may be expressed by chromaticity.

The display format setting unit 74 sets a display format of images in the screen when any one of the B-mode images represented by the plural kinds of image data stored in the image memory 24, the synthesized B-mode image or the synthesized image of the B-mode image and the Doppler image is displayed in the display unit 26.

An ultrasonic observation method according to the seventh embodiment of the present invention will be explained by referring to FIGS. 18-22. The ultrasonic observation method according to the embodiment is a method of generating B-mode images and Doppler images, and can be used in the ultrasonic observation apparatus shown in FIG. 18.

First, in the ultrasonic endoscope shown in FIG. 18, the angular interval between adjacent ultrasonic beams is set to 90° (=360°/4), and the transmission apertures, transmission focus, reception apertures, reception focus and image areas are set based on the following information stored in the transmission beam information storage unit 140 (FIG. 1).

Beam 1 (TB23): frequency of 4 MHz, aperture width of 6.4 mm, focal distance of 8 cm Beam 2 (TB24): frequency of 4 MHz, aperture width of 6.4 mm, focal distance of 8 cm Beam 3 (TB25): frequency of 4 MHz, aperture width of 6.4 mm, focal distance of 8 cm Beam 4 (TB26): frequency of 7.5 MHz, aperture width of 4.8 mm, focal distance of 4 cm The ultrasonic beams TB23 to TB25 are used for generating Doppler images.

Figure 20:
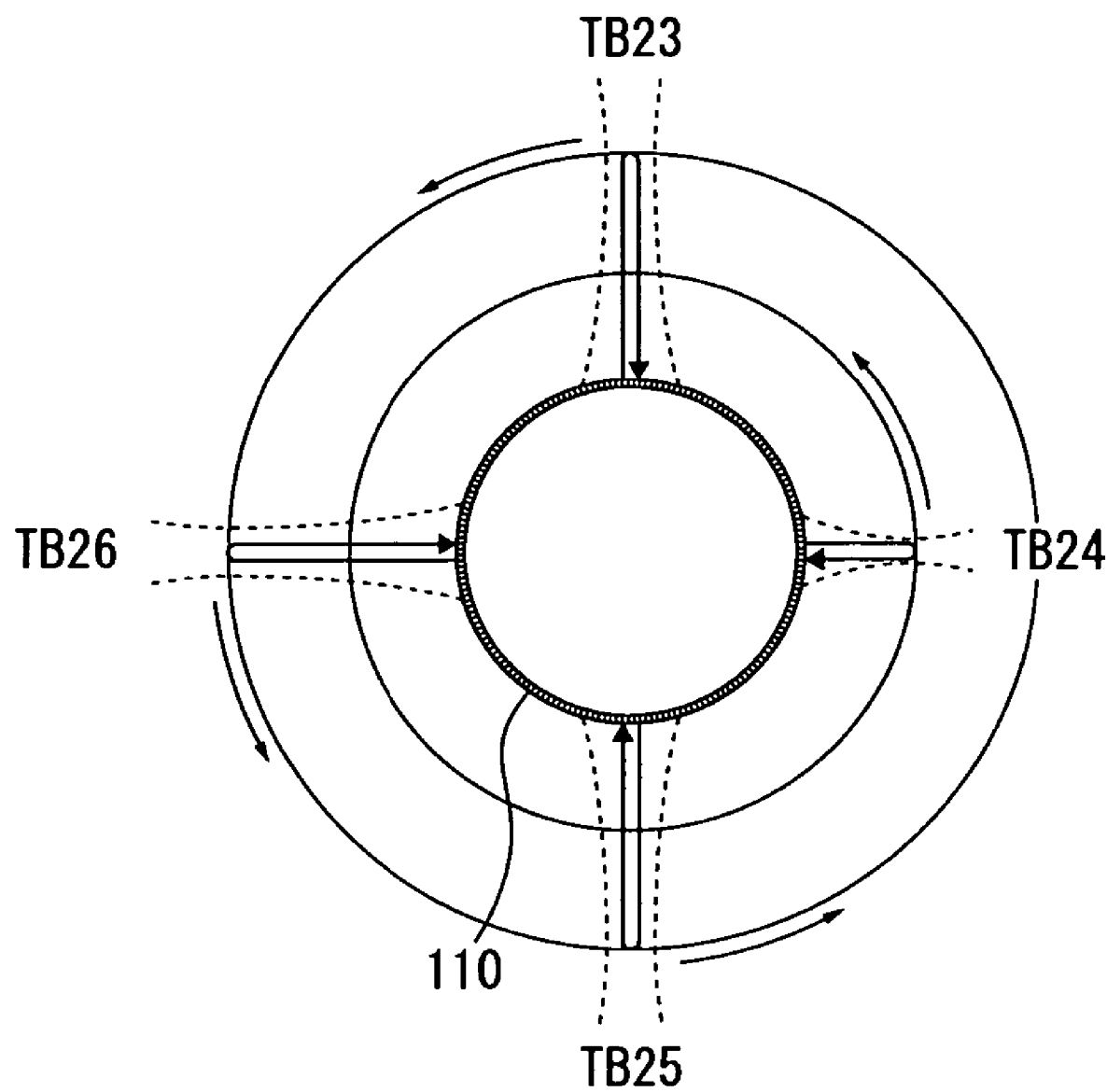
FIG. 20 is a schematic diagram showing a state in which ultrasonic beams are transmitted and received in the constitution of an ultrasonic observation apparatus according to the seventh embodiment of the present invention.

Thereby, as shown in FIG. 20, ultrasonic beams TB23 to TB26 are transmitted and an angle range of 360° around the ultrasonic transducer unit 110 is scanned.

The ultrasonic beams TB1 to TB4 transmitted from the ultrasonic transducer unit 110 and reflected from the object are received by the set reception apertures. The reception signals outputted from the respective reception apertures are subjected to the processing in the reception signal processing unit 20 in the same way as has been explained in the first embodiment.

In the sound ray data processing unit 71, the sound ray data corresponding to the ultrasonic beams TB23 to TB25 at 4 MHz are outputted to the Doppler processing unit 72, and subjected to predetermined processing. Thereby, Doppler image data is generated and outputted to the image synthesizing unit 23. On the other hand, in the sound ray data processing unit 71, the sound ray data corresponding to the ultrasonic beam TB26 at 7.5 MHz is outputted to the B-mode image data generating unit 22. Thereby, B-mode image data is generated.

Figure 21:
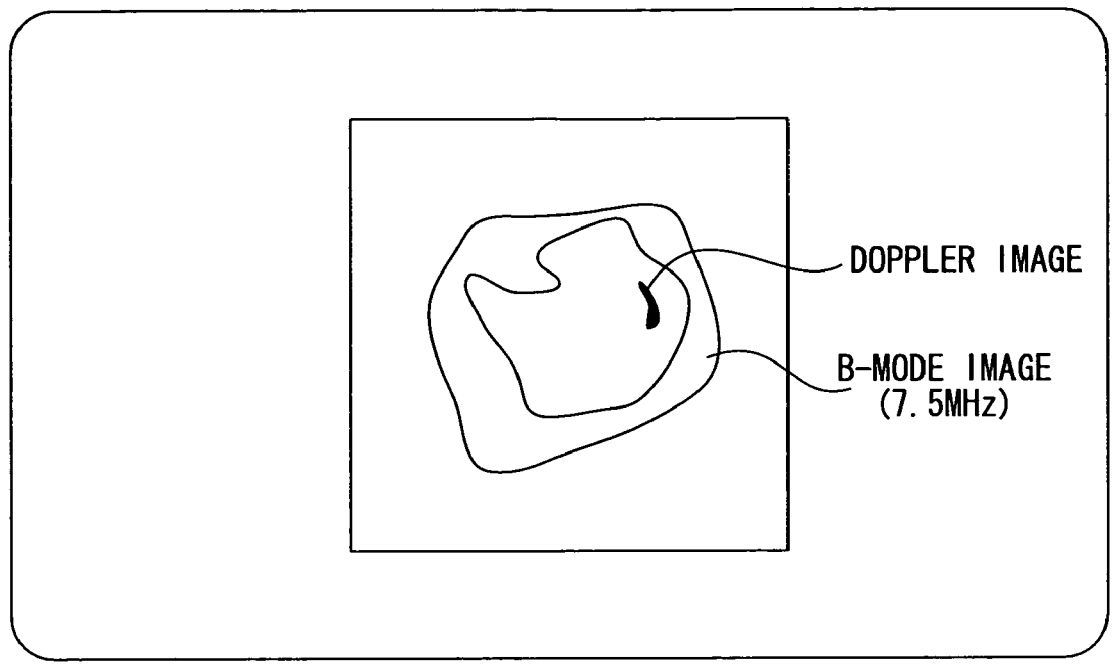
FIG. 21 is a schematic diagram showing an example of an image display format set by a display format setting unit as shown in FIG. 18.
Figure 22:
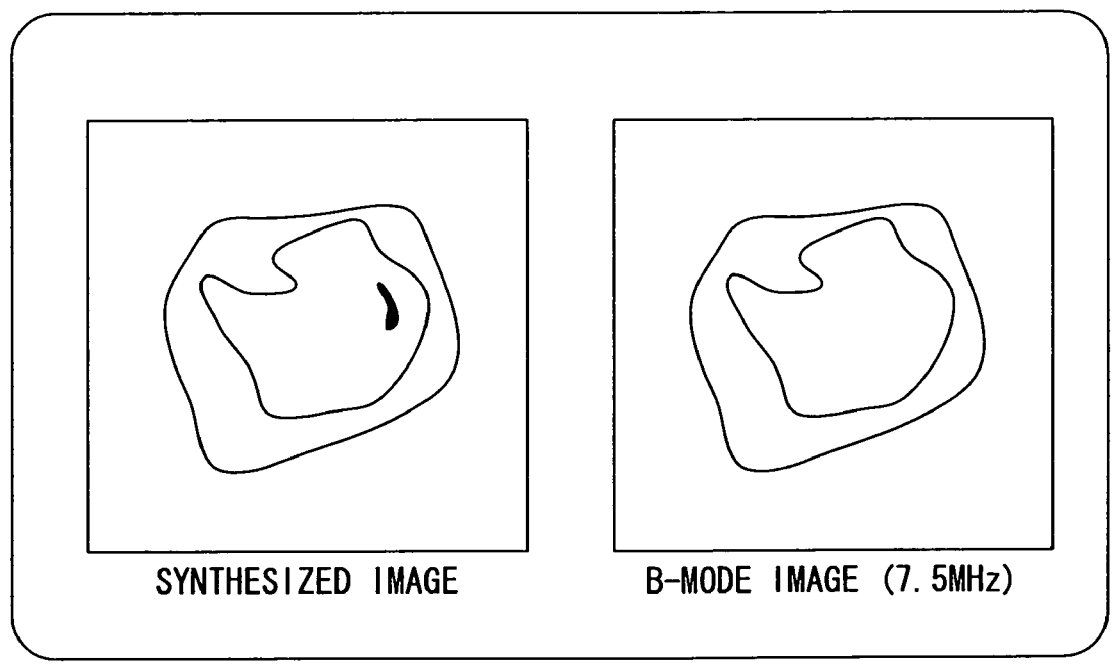
FIG. 22 is a schematic diagram showing another example of an image display format set by the display format setting unit as shown in FIG. 18.

As the display format set by the display format setting unit 74, a format in which the synthesized image is singly displayed as shown in FIG. 21, or a format in which the synthesized image and a normal B-mode image or the Doppler image are displayed side-by-side as shown in FIG. 22 may be used.

Although the B-mode image is generated by using only the sound ray data corresponding to the ultrasonic beam TB4 at 7.5 MHz in the embodiment, the B-mode image may be generated by using the sound ray data corresponding to one of the ultrasonic beams TB23 to TB25 at 4 MHz, or the synthesized B-mode image may be generated by using the sound ray data corresponding to the ultrasonic beams TB23 to TB25 at 4 MHz.

Thus, according to the embodiment, conditions of frequencies, focal depths and so on can be respectively set with respect to plural ultrasonic beams to be substantially simultaneously transmitted, and therefore, normal B-mode images and Doppler images can be generated based on the ultrasonic image information acquired under the best conditions. Further, since plural ultrasonic beams are secured for Doppler image generation, the reduction of frame rate can be prevented. Furthermore, since the user can select the display format of a synthesized image of the B-mode image and the Doppler image or a normal B-mode image according to preference, diagnostic efficiency can be raised in the sites of medical diagnoses.

Next, an ultrasonic observation apparatus according to the eighth embodiment of the present invention will be explained by referring to FIGS. 23 and 24.

Figure 23:
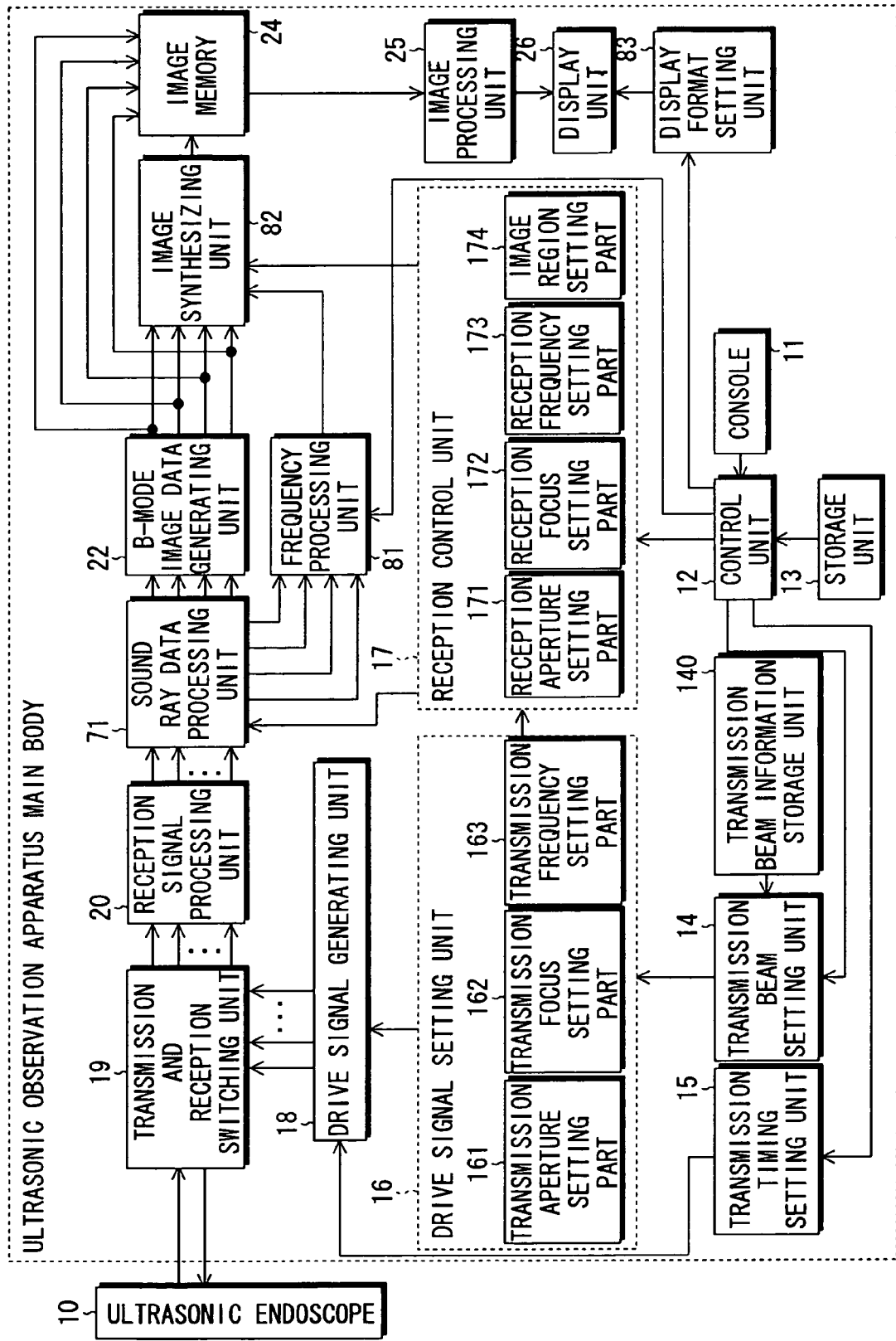
FIG. 23 is a block diagram showing a constitution of an ultrasonic observation apparatus according to the eighth embodiment of the present invention.
Figure 24:
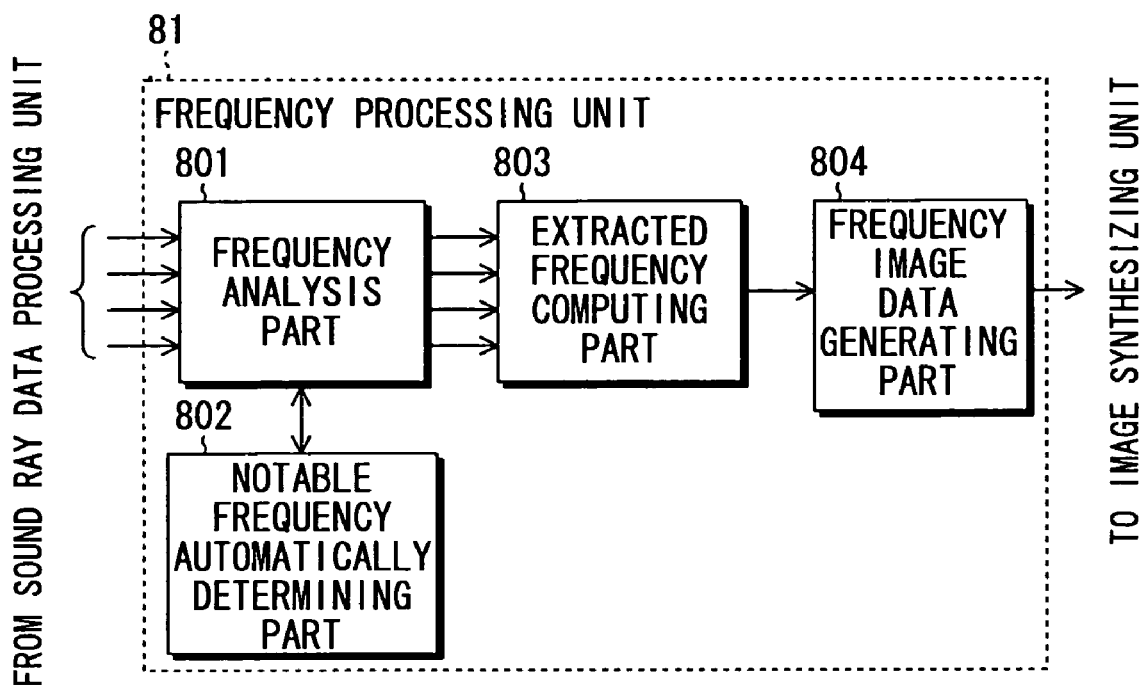
FIG. 24 is a block diagram showing a constitution of a frequency processing unit shown in FIG. 23.

As shown in FIG. 23, compared to the ultrasonic observation apparatus main body shown in FIG. 18, the ultrasonic observation apparatus according to the eighth embodiment includes a frequency processing unit 81, an image synthesizing unit 82 and a display format setting unit 83 in place of the Doppler processing unit 72, the image synthesizing unit 73 and the display format setting unit 74 shown in FIG. 18. Other constitution is the same as that of the ultrasonic observation method shown in FIG. 18.

The frequency processing unit 81 generates frequency subtraction image data representing subtraction images of plural ultrasonic images acquired based on frequencies different from one another. FIG. 24 shows a constitution of the frequency processing unit 81 shown in FIG. 23. The frequency processing unit 81 includes a frequency analysis part 801, a notable frequency automatically determining part 802, an extracted frequency computing part 803 and a frequency image data generating part 804.

The frequency analysis part 801 calculates plural frequency components included in the sound ray data outputted form the respective data processing systems of the sound ray data processing unit 71 by FFT (fast Fourier transform).

The notable frequency automatically determining part 802 automatically determines at least one notable frequency component from among those frequency components. For example, the notable frequency automatically determining part 802 may determine components having predetermined frequencies as notable frequency components, may determine frequency components with high intensity as notable frequency components, or may determine frequency components having large peaks or dips in all or a part of the region in the depth direction of the object as notable frequency components.

Here, by determining frequency components based on features on frequency characteristics of a particular tissue in a part with higher ultrasonic echo intensity, the particular tissue can be displayed with more emphasis. On the other hand, by determining frequency components by focusing attention on a part with lower ultrasonic echo intensity, speckle components resulting from addition and interference among a large number of weak echoes can be reduced. In either case, S/N ratio can be improved. Further, in the case where the relative values of plural frequency components are calculated, a two-dimensional distribution of a particular tissue can be obtained accurately based on the relative values.

The extracted frequency computing part 803 inputs the at least one notable frequency component determined by the notable frequency automatically determining part 802 from the frequency analysis part 801, and perform correction of frequency characteristics in the transmission and reception of ultrasonic waves by the ultrasonic transducers and so on. Here, the ultrasonic echo intensity can be obtained more accurately in the case where the frequency characteristics in the transmission and reception of ultrasonic waves by the ultrasonic transducers have been stored in the storage unit 13 and the extracted frequency computing part 803 corrects the intensity of at least one frequency component inputted from the frequency analysis part 801.

Such processing of the extracted frequency computing part 803 is performed on the reception data outputted from the plural signal processing systems of the sound ray data processing unit 71.

Furthermore, the extracted frequency computing part 803 calculates, based on the analysis results of reception data outputted from the plural signal processing systems of the sound ray data processing unit 71 (i.e., data acquired by ultrasonic beams having different frequencies), differences between them (differences between reception data values) as relative relationships of intensity of plural frequency components. Alternatively, ratios may be calculated as relative relationships. Further, more information can be obtained in the case where not only the frequency components of the reception signals, but also phase components are extracted and utilized for ultrasonic image generation.

The frequency image data generating part 804 generates frequency image data based on the data outputted from the extracted frequency computing part 803. The frequency image data represents a frequency subtraction image and can be used when tissue properties are discriminated in medical diagnoses. The frequency image data is outputted to the image synthesizing unit 82 shown in FIG. 23.

The image synthesizing unit 82 generates synthesized B-mode image data representing a synthesized B-mode image formed by synthesizing plural B-mode images based on plural kinds of B-mode image data generated in the B-mode image data generating unit 22, and generates synthesized image data representing a synthesized image of any one of the B-mode images or the synthesized B-mode image and the frequency subtraction image. In the synthesized image, the B-mode image or the synthesized B-mode image may be expressed by brightness and the frequency subtraction image may be expressed by chromaticity.

The display format setting unit 83 sets a display format of images in the screen when displaying any one of the B-mode images represented by the plural kinds of image data stored in the image memory 24, the synthesized B-mode image, the frequency subtraction image or a synthesized image of the B-mode image and the frequency subtraction image in the display unit 26. As a display format, various formats such as a format in which the synthesized image is singly displayed and a format in which the synthesized image and the synthesized B-mode image are displayed side-by-side are cited.

Thus, according to the embodiment, since the frequency images are generated based on the sound ray data acquired by frequency, S/N ratio is improved compared to a general method using sound ray data acquired based on wideband pulses. Therefore, for example, in the case where tissue properties of an observation part using frequency subtraction images, the accuracy of diagnoses can be raised.

Next, an ultrasonic observation apparatus according to the ninth embodiment of the present invention will be explained by referring to FIG. 25.

Figure 25:
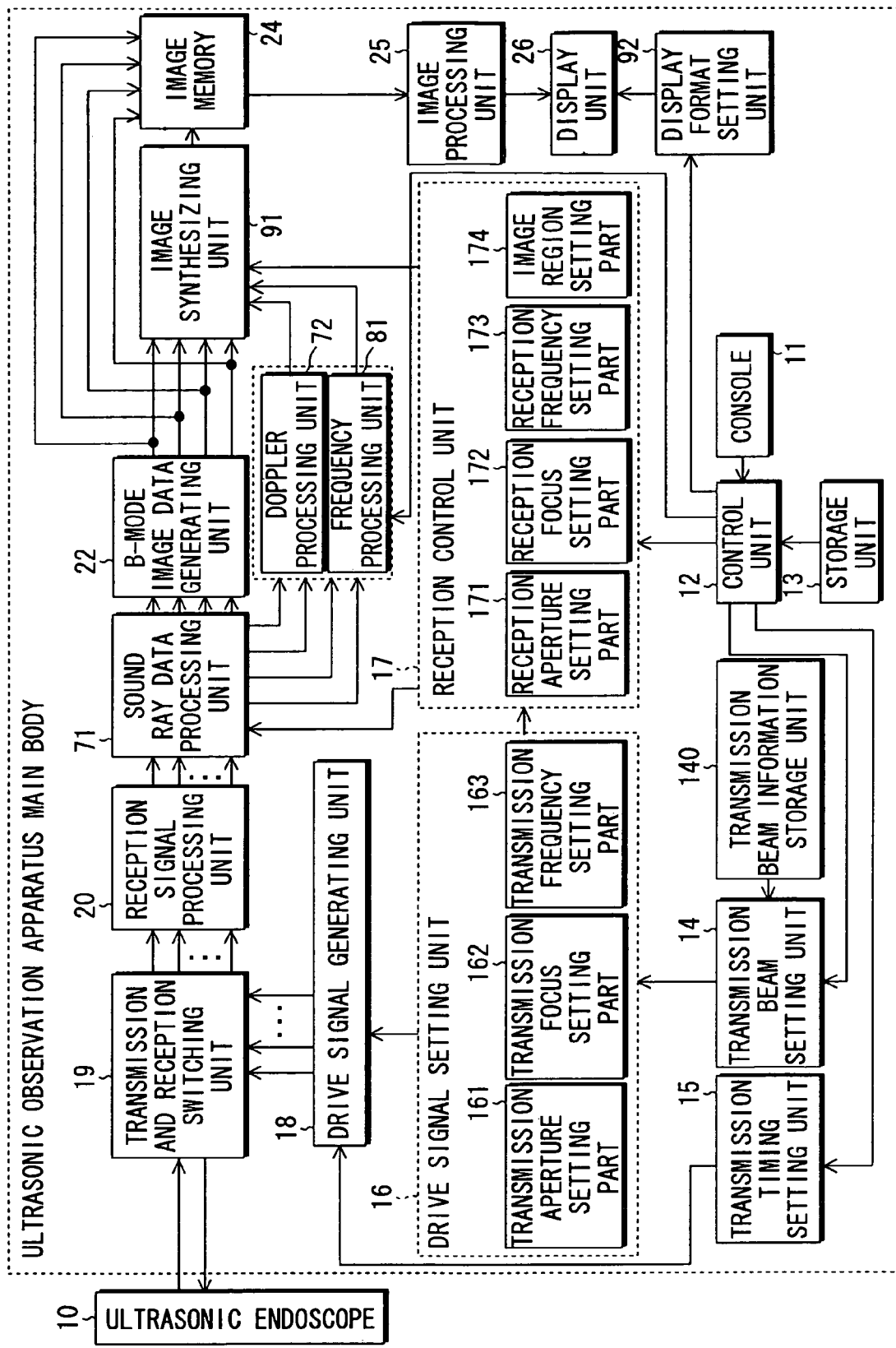
FIG. 25 is a block diagram showing a constitution of an ultrasonic observation apparatus according to the ninth embodiment of the present invention.

As shown in FIG. 25, compared to the ultrasonic observation apparatus main body shown in FIG. 18, the ultrasonic observation apparatus according to the ninth embodiment further includes the frequency processing unit 81 and includes an image synthesizing unit 91 and a display format setting unit 92 in place of the image synthesizing unit 73 and the display format setting unit 74 shown in FIG. 18. Other constitution is the same as that of the ultrasonic observation method shown in FIG. 18. Further, the constitution and operation of the frequency processing unit 81 are the same as those have been explained in the eighth embodiment.

In the ninth embodiment, the image synthesizing unit 91 generates synthesized B-mode image data representing a synthesized B-mode image based on B-mode images generated by the B-mode image data generating unit 22, and generates synthesized image data representing a synthesized image of any one of the B-mode images or the synthesized B-mode image and the Doppler image and/or the frequency subtraction image. In the synthesized image, the B-mode image or the synthesized B-mode image may be expressed by brightness and the Doppler image and/or frequency subtraction image may be expressed by chromaticity. The display format setting unit 92 sets a display format of images in the screen when displaying plural kinds of B-mode images, the synthesized B-mode image, the Doppler image, the frequency subtraction image or a synthesized image thereof in the display unit 26. Various formats such as a format in which the synthesized image is singly displayed and a format in which the synthesized image and the synthesized B-mode image are displayed side-by-side are cited as a display format.

According to the embodiment, various kinds of ultrasonic images can be generated and displayed according to diagnostic purposed and user's preferences, and therefore, diagnostic efficiency and diagnostic accuracy can be improved.

In the above-mentioned first to ninth embodiments, electronic radial scan is performed by using ultrasonic transducer unit including plural ultrasonic transducers arranged on the circumference. However, electronic radial scan may be performed by using a convex ultrasonic transducer array fabricated by arranging ultrasonic transducers on a circular arc.

Further, in the above-mentioned first to ninth embodiments, the case where four ultrasonic beams are simultaneously transmitted has been principally explained. However, the number of ultrasonic beams to be simultaneously transmitted can be changed to a desired number. Naturally, the number of ultrasonic beams may be set to one and single beam transmission may be performed. Although the upper limit of the ultrasonic beams is not specifically limited, the larger the number of ultrasonic beams, the narrower the angular interval between adjacent ultrasonic beams becomes, and crosstalk easily occurs. Accordingly, the number of ultrasonic beams is desirably one to four. In the case where the number of ultrasonic beams is four, crosstalk relatively hardly occurs because the angular interval between adjacent ultrasonic beams becomes 90°.

Furthermore, in the above-mentioned first to ninth embodiments, the reception signals outputted from the respective ultrasonic transducers are converted into digital signals, and then, distributed to the plural signal processing systems (FIG. 5) corresponding to the reception apertures or transmission apertures. However, the reception signals as analog signals may be distributed to the signal processing systems corresponding to the reception apertures.

The invention claimed is:

1. An ultrasonic observation apparatus for acquiring ultrasonic image information on an object to be inspected by scanning the object in a body cavity thereof according to one of a radial scan method and a convex scan method so as to generate an ultrasonic image based on the ultrasonic image information, said apparatus comprising:

an ultrasonic endoscope including plural ultrasonic transducers, arranged on one of a circumference and a circular arc, configured to generate ultrasonic waves according to drive signals applied thereto and receive the reflected ultrasonic waves to output reception signals, respectively;

transmission aperture setting means for setting, from among said plural ultrasonic transducers, plural ultrasonic transducer groups for respectively transmitting plural ultrasonic beams in directions different from one another as plural transmission apertures;

transmission frequency setting means for setting frequencies of drive signal groups to be supplied to the plural ultrasonic transducer groups set as said plural transmission apertures;

transmission timing setting means for changing pulse repetition frequencies of the drive signal groups according to the frequencies of the drive signal groups to be supplied to the plural ultrasonic transducer groups set as said plural transmission apertures;

drive signal generating means for generating the drive signal groups having the frequencies set by said transmission frequency setting means and the pulse repetition frequencies set by said transmission timing setting means to supply the drive signal groups to the plural ultrasonic transducer groups set as said plural transmission apertures;

reception aperture setting means for setting plural ultrasonic transducer groups as plural reception apertures corresponding to said plural transmission apertures;

signal processing means for performing signal processing on reception signal groups respectively outputted from the plural ultrasonic transducer groups set as said plural reception apertures; and control means for controlling said transmission aperture setting means to sequentially change regions of the plural ultrasonic transducer groups to be set as said plural transmission apertures at a predetermined time interval, wherein:

said transmission timing setting means lowers a pulse repetition frequency of a drive signal group having a lower frequency than that of a drive signal group having a higher frequency; and said control means controls said transmission aperture setting means such that scan density of an ultrasonic beam having the lower frequency becomes lower than that of an ultrasonic beam having the higher frequency so as to keep an angular interval between the ultrasonic beam having the lower frequency and the ultrasonic beam having the higher frequency within a predetermined range.

2. An ultrasonic observation apparatus according to claim 1, further comprising:
    filter processing means for performing bandpass filter processing, which corresponds to the plural different frequencies of the drive signal groups to be supplied to the plural ultrasonic transducer groups set as said plural transmission apertures, on the reception signal groups respectively outputted from the plural ultrasonic transducer groups set as said plural reception apertures.

3. An ultrasonic observation apparatus according to claim 1, wherein said reception aperture setting means sets, as said plural reception apertures, plural ultrasonic transducer groups respectively including the plural ultrasonic transducer groups set as said plural transmission apertures.

4. An ultrasonic observation apparatus according to claim 1, wherein said signal processing means performs reception focus processing on the reception signal groups to generate plural sound ray signals representing ultrasonic image information on ultrasonic beams having focal points formed at depths set with respect to said plural reception aperture.

5. An ultrasonic observation apparatus according to claim 4, further comprising:
    B-mode image generating means for generating plural kinds of B-mode image data respectively representing plural B-mode images corresponding to the plural sound ray signals.

6. An ultrasonic observation apparatus according to claim 5, further comprising:
    correcting means for correcting gain and/or gradation of the plural B-mode images.

7. An ultrasonic observation apparatus according to claim 6, wherein said correcting means corrects the gain and/or gradation such that density ranges in the plural B-mode images becomes equal to one another.

8. An ultrasonic observation apparatus according to claim 5, further comprising:
    display format setting means for setting a display format for displaying at least one B-mode image selected from among the plural B-mode images.

9. An ultrasonic observation apparatus according to claim 5, further comprising:
    image synthesizing means for generating synthesized B-mode image data representing a synthesized image formed by synthesizing the plural B-mode images; and
    image area setting means for setting at least one image area composing the synthesized image with respect to each of the plural B-mode images.

10. An ultrasonic observation apparatus according to claim 9, wherein said image area setting means sets the at least one image area based on one of a frequency of a drive signal group and a focal depth set by said reception focus means with respect to each of the plural B-mode images.

11. An ultrasonic observation apparatus according to claim 4, further comprising:
    Doppler image generating means for generating Doppler image data representing a Doppler image based on at least one sound ray signal generated by said signal processing means.

12. An ultrasonic observation apparatus according to claim 11, further comprising:
    means for generating harmonic image data representing a harmonic image based on at least one sound ray signal generated by said signal processing means.

13. An ultrasonic observation apparatus according to claim 12, wherein said transmission frequency setting means sets the plural different frequencies to (i) at least one drive signal group corresponding to at least one reception signal group to be used for generating a Doppler image, (ii) at least one drive signal group corresponding to at least one reception signal group to be used for generating a harmonic image, and (iii) at least one drive signal group corresponding to at least one reception signal group to be used for generating a B-mode image.

14. An ultrasonic observation apparatus according to claim 11, wherein said transmission frequency setting means sets the plural different frequencies to (i) at least one drive signal group corresponding to at least one reception signal group to be used for generating a Doppler image and (ii) at least one drive signal group corresponding to at least one reception signal group to be used for generating a B-mode image.

15. An ultrasonic observation apparatus according to claim 4, further comprising:
    means for generating harmonic image data representing a harmonic image based on at least one sound ray signal generated by said signal processing means.

16. An ultrasonic observation apparatus according to claim 15, wherein said transmission frequency setting means sets the plural different frequencies to (i) at least one drive signal group corresponding to at least one reception signal group to be used for generating a harmonic image and (ii) at least one drive signal group corresponding to at least one reception signal group to be used for generating a B-mode image.

17. An ultrasonic observation apparatus according to claim 4, further comprising:
    subtraction processing means for generating frequency subtraction image data representing a frequency subtraction image based on said plural sound ray signals; and
    display format setting means for setting a display format for displaying both a B-mode image and the frequency subtraction image on said display means.

18. An ultrasonic observation apparatus according to claim 1, further comprising:
    transmission focus processing means for setting delay times provided to respective drive signals included in each of the drive signal groups supplied by said drive signal generating means with respect to said plural transmission apertures such that the ultrasonic beams respectively transmitted from said plural transmission apertures form focal points at predetermined depths.

19. An ultrasonic observation apparatus according to claim 1, wherein said transmission aperture setting means sets aperture widths different from one another with respect to said plural transmission apertures.

20. An ultrasonic observation apparatus according to claim 1, wherein said transmission aperture setting means sets positions of said plural transmission apertures such that angular intervals between adjacent two ultrasonic beams to be transmitted in different directions become equal to one another.

21. An ultrasonic observation apparatus according to claim 20, wherein said transmission aperture setting means sets positions of four transmission apertures such that four ultrasonic beams transmitted from said four transmission apertures form an angle of 90° with one another.

22. An ultrasonic observation apparatus according to claim 1, wherein said drive signal generating means generates drive signal groups having frequencies within a range from 4 MHz to 20 MHz.

23. An ultrasonic observation apparatus according to claim 1, wherein said transmission aperture setting means changes a number of transmission apertures, and/or said transmission frequency setting means changes the frequencies of the drive signal groups for said plural transmission apertures.

24. An ultrasonic observation apparatus according to claim 1, wherein said control means sequentially changes regions of the ultrasonic transducer groups set as said plural transmission apertures within a range of one of the circumference and the circular arc determined according to a number of transmission apertures.

25. An ultrasonic observation apparatus according to claim 1, wherein said control means controls said transmission aperture setting means and said transmission frequency setting means to scan the object such that the scan density of the ultrasonic beam having the lower frequency becomes lower than that of the ultrasonic beam having the higher frequency and then scan regions, which have not been scanned with the ultrasonic beam having the lower frequency, with the ultrasonic beam having the lower frequency.

* * * * *